US009565857B2

(12) United States Patent
Raad et al.

(10) Patent No.: US 9,565,857 B2
(45) Date of Patent: Feb. 14, 2017

(54) ANTIMICROBIAL SOLUTIONS

(75) Inventors: Issam Raad, Missouri City, TX (US); George Abiaad, Chino Hills, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/821,546

(22) PCT Filed: Sep. 9, 2011

(86) PCT No.: PCT/US2011/051020

§ 371 (c)(1),
(2), (4) Date: May 21, 2013

(87) PCT Pub. No.: WO2012/034032

PCT Pub. Date: Mar. 15, 2012

(65) Prior Publication Data

US 2013/0231302 A1 Sep. 5, 2013

Related U.S. Application Data

(60) Provisional application No. 61/381,766, filed on Sep. 10, 2010.

(51) Int. Cl.

| | |
|---|---|
| ***A01N 47/44*** | (2006.01) |
| ***A01N 43/16*** | (2006.01) |
| ***A01N 31/14*** | (2006.01) |
| ***A61K 31/715*** | (2006.01) |
| ***A61K 31/155*** | (2006.01) |
| ***A61K 31/085*** | (2006.01) |
| ***A61L 2/18*** | (2006.01) |
| ***A61L 29/16*** | (2006.01) |
| ***A01N 31/02*** | (2006.01) |

(52) U.S. Cl.

CPC ............... *A01N 47/44* (2013.01); *A01N 31/02* (2013.01); *A01N 31/14* (2013.01); *A01N 43/16* (2013.01); *A61K 31/085* (2013.01); *A61K 31/155* (2013.01); *A61K 31/715* (2013.01); *A61L 2/186* (2013.01); *A61L 29/16* (2013.01); *A61L 2202/24* (2013.01); *A61L 2300/206* (2013.01); *A61L 2300/404* (2013.01)

(58) Field of Classification Search

CPC ........ A01N 47/44; A01N 43/16; A01N 31/14; A01N 2300/00; A61K 31/715; A61K 31/155; A61K 31/085

USPC ................................ 514/635, 54; 206/524.1

See application file for complete search history.

(56) References Cited

U.S. PATENT DOCUMENTS

| | | | | |
|---|---|---|---|---|
| 4,748,158 | A | 5/1988 | Biermann et al. | |
| 5,000,867 | A | 3/1991 | Heinhuis-Walther et al. | |
| 5,362,754 | A | 11/1994 | Raad et al. | |
| 5,670,160 | A | 9/1997 | Diehl et al. | |
| 5,688,516 | A | 11/1997 | Raad et al. | |
| 6,340,663 | B1 * | 1/2002 | Deleo et al. | 510/438 |
| 2005/0013836 | A1 * | 1/2005 | Raad | 424/400 |
| 2006/0009369 | A1 * | 1/2006 | Kilkenny | A01N 33/12 510/504 |
| 2008/0175811 | A1 * | 7/2008 | Kritzler | 424/78.07 |
| 2009/0324738 | A1 | 12/2009 | Krongauz | |
| 2010/0160201 | A1 | 6/2010 | Scheuing et al. | |
| 2010/0222433 | A1 | 9/2010 | Ren et al. | |
| 2012/0201902 | A1 * | 8/2012 | Modak et al. | 424/618 |

FOREIGN PATENT DOCUMENTS

| | | |
|---|---|---|
| EP | 1146112 | 10/2001 |
| WO | WO 2006/122345 | 11/2006 |

OTHER PUBLICATIONS

Glossary of medical education terms, Institute of International Medical Education. http://www.iime.org/glossary.htm Accessed in Mar. 2013.*

Simoes et al. A review of current and emergent biofilm control strategies. Food Sci Technol 43:573-583, 2010.*

Endo et al. Antimicrobial Activity of Tertiary Amine Covalently Bonded to a Polystyrene Fiber. Appl Environ Microbiol 2050-2055, 1987.*

Cognis Carechemicals. Alkyl Polyglucosides(APG®)Benefits of Glucopone®-Types in Hard Surface Cleaning. p. 1-44, Apr. 2005. http://www.ccindustrial.cl/ayuda/alkyl_polyglucosides.pdf.*

PCT International Preliminary Report on Patentability issued in International Application No. PCT/US2011/051020, issued Mar. 12, 2013.

PCT International Search Report and Written Opinion issued in International Application No. PCT/US2011/051020, mailed Jun. 29, 2012.

* cited by examiner

*Primary Examiner* — Clinton Brooks
*Assistant Examiner* — Yih-Horng Shiao
(74) *Attorney, Agent, or Firm* — Parker Highlander PLLC

(57) ABSTRACT

The present invention provides antimicrobial solutions that in certain cases comprise a biguanide and a glycol ether and, in some cases, optionally also includes combinations of at least one an alcohol, at least one chelator, glycerol, deoxycholate, and/or at least one alkylpolyglucoside. In certain aspects the invention comprises a biguanide and deoxycholate or a combination of chelator, ethanol, and alkylpolyglucoside. Also provided are methods for rapidly killing and/or reducing bacteria, fungi, or virus from surfaces, for example, including surfaces of indwelling medical devices and organic surfaces such as skin and sutures, and inorganic surfaces such as medical equipment, pipelines etc.

21 Claims, 10 Drawing Sheets

ANTIMICROBIAL SOLUTIONS

This application is a national phase application under 35 U.S.C. 371 of International Application No. PCT/US2011/051020, filed Sep. 9, 2011, which claims priority to U.S. Provisional Patent Application Ser. No. 61/381,766, filed Sep. 10, 2010. The entire text of each of the above referenced disclosures is specifically incorporated herein by reference.

BACKGROUND OF THE INVENTION

1. Field of the Invention

The present invention relates generally to the fields of medicine and microbiology. More particularly, it concerns methods of reducing microbial organisms from surfaces, including indwelling medical devices, medical equipment and other surfaces, for example.

2. Description of Related Art

With the widespread of infectious diseases at the global level, the use of highly effective and safe disinfectants has been the number one public health challenge around the globe. Most of the infectious diseases that are associated with high morbidity and mortality are transmitted through skin contact or contact with a colonized surface in the environment. This includes highly resistant bacterial organisms, which is becoming a widely spread community organism, such as, for example, methicillin-resistant *Staphylococcus aureus* (MRSA) or other resistant bacteria, fungi, viruses (such as the H1N1 and SARS, for example) as well as other parasitic pathogens. Unfortunately, the currently widely used disinfectants in various settings, including hospitals, daycare centers, and other places that host high-risk individuals, are marred by several disadvantages, particularly being hazardous in terms of their toxicity, instability and the potential health risks to the users. None of the currently widely used chemical disinfectants is ideal in terms of its safety, lack of toxicity and broad-spectrum activity against various pathogens.

Chlorine Bleach Solutions

Household and institutional chlorine bleaches contain 5.25% active sodium hypochlorite when they are manufactured. The remaining 94.75% is primarily water. Chlorinated compounds such as sodium hypochlorite when diluted in water form hypochlorous acid. This acid is extremely effective against many types of microorganisms including bacteria, fungi and viruses. For instance, the product label for Purex household bleach claims it is effective against *Staphylococcus* and *Streptococcus* bacteria, Influenza A and B viruses and athletes foot fungus. However, the label also says a surface must be pre-cleaned before using the chlorine bleach solution.

There are disadvantages of using chlorine bleach as a disinfectant. Many institutions do not commonly use chlorine bleach products because of the following: 1. lacks detergency—they contain no wetting agents to allow the disinfecting agent to penetrate soils, so surfaces must be pre-cleaned before the chlorine bleach will effectively kill germs; 2. very caustic to human tissues—can burn skin and eyes; 3. reacts with other chemicals to create toxic byproducts and gases—incompatible with products that contain ammonia, hydrochloric acid, phosphoric acid and acetic acid (vinegar); 4. fumes can be irritating—occupants of buildings frequently complain about bleach and bleach-related odors migrating into their work areas; 5. can emit a carcinogenic gas if it comes in contact with formaldehyde, or is hyperchlorinated by hot water; 6. extremely corrosive to metals—Chlorine bleach can attack and corrode metal surfaces as well as permanently discolor countertops; 7. discolor fibers and colored surfaces—carpets, entrance matting and clothing are just a few of the fibers that can be damaged when contacted by chlorine bleach solutions; 8. damage floor finishes—Chlorine bleach can attack the floor finish coatings on the floor requiring them to be removed and replaced; 9. rapidly inactivated by organic debris (blood, tissue, saliva, microbes); 10. diluted solutions quickly lose their effectiveness. Chlorine bleach is unstable and can lose its oxidizing and disinfecting strength rapidly compared to "quat" based disinfectant-cleaners and/or sanitizers.

Phenolics Based Solutions

Phenols or phenolic disinfectant-cleaners are not as corrosive as chlorine bleach. But they are aggressive enough to attack and damage floor finishes and sensitive flooring. Phenolic disinfectants are still the preferred product in a few health care facilities. They are used in areas where gross contamination of blood and body fluids subsist. Phenolics are effective against pathogenic bacteria like tubercle *bacillus* that cause tuberculosis. There are disadvantages of phenolic disinfectants and many institutions do not commonly use phenolic products because of the following: 1. can be toxic to skin and eyes (depigmentation can occur with long periods of exposure or use); 2. commonly causes sinus and respiratory tract irritation or problems; 3. corrosive to certain rubber and plastic surfaces; 4. Flammable; 5. can leave a film on a cleaned surface, creating a buildup that will eventually need removal; 6. solutions need to be discarded and remixed daily; and 7. Expensive.

Quaternary Ammonium Chlorides

Quarternary ammonium chlorides or "quats" as they are commonly known are based upon the active ingredient benzalkonium chloride. These quaternary salt compounds can be formulated with a variety of ingredients to provide a safe and effective neutral pH, disinfectant-cleaner without damaging floor finishes or sensitive floor surfaces. Quats are effective in destroying a broad spectrum of harmful microorganisms. They are effective in killing many pathogenic microorganisms while cleaning the surfaces upon which they reside—all in one simple step. There are disadvantages of quaternary ammonium chlorides as follows: 1. quaternary ammonium chlorides do not kill tuberculosis; 2. do not perform especially well when challenged by organic soil. Quaternary ammonium chlorides do not provide residual activity on hard surfaces. The biggest single problem with the use of quaternary ammonium chlorides is their inconsistent efficacy against moulds, particularly *Aspergillus;* 3. quaternary ammonium chlorides have also had trouble with ever-present microorganisms such as *E. coli* and *Pseudomonas;* 4. quaternary ammonium chlorides have been suspected in developing microorganism's resistance to QAC quaternary ammonium chlorides after long periods of reappeared use.

Alcohols (Such as Ethyl and Isopropyl Alcohol, for Example)

Ethanol and Isopropyl alcohol are both excellent disinfectants whose germicidal properties are generally underestimated. Both are rapidly bactericidal against vegetative bacterial forms, tuberculocidal, fungicidal, and virucidal. The disinfectant properties of both ethanol and isopropyl alcohol rapidly drop at concentrations below fifty percent (50%) and above ninety percent (90%). The recommended concentration for use is sixty-ninety percent (60-90%) by volume. There are disadvantages of alcohols, as follows: 1. both ethanol and isopropyl alcohol are volatile and flammable compounds and must only be used with adequate ventilation; 2. alcohols, in general, are destructive to rubber compounds and to most of the cement and glues used in instruments, especially optics.

Thus, there is a considerable need for better and improved antimicrobial compositions.

SUMMARY OF THE INVENTION

The present invention overcomes these and other limitations in the art and provides compositions that reduce or eradicate microbial agents from surfaces, for example. In particular aspects of the invention, there are methods and/or compositions for antimicrobial activity. More particular, the present invention regards combinations of compounds for antimicrobial activity. In specific cases, the present invention concerns methods and compositions related to one or more guanidium compounds and one or more glycol ethers, optionally with an additional agent. Exemplary additional agents include one or more alkyl polyglycosides, one or more alcohols, deoxycholate, one or more chelators, and/or glycerol. The compositions are suitable for antimicrobial activity on any surface, including any organic or inorganic surface.

In certain embodiments, the antimicrobial composition of the invention is employed for the following: 1) environmental disinfectant; 2) skin and/or mucosal sanitizer; 3) pipeline; and 4) lock solution for catheters.

In particular embodiments of the invention, there is an environmental disinfectant or an oral or skin sanitizer with active disinfectant activity. In certain aspects the present invention regards a germicidal disinfectant for wide use that inactivates virtually all recognized pathogenic microorganisms. In specific embodiments, the disinfectant has rapid decontaminating activity resulting in the killing of organisms and the removal of the contamination after use with no quantitative implication.

In specific embodiments, the present invention concerns novel, environmentally safe, and highly effective disinfectant chlorhexidine in combination with bioenhancing surfactants and detergents. In specific embodiments, the detergents include an alkyl polyglycoside, such as Glucopon®, a glycol ether, such as 2-(2-ethoxyethoxy)ethanol (Dowanol®; The Dow Chemical Company, Midland, Mich.) and/or deoxycholate, for example.

In particular aspects of the invention, there are combinations of guanidium compounds (such as chlorhexidine) with one or more bioenhancers, such as Dowanol. In certain embodiments, surfactants such as Glucopon® and/or detergent such as deoxycholate further enhances the activity of the combination of chlorhexidine and Dowanol, for example. In certain cases, Dowanol® is an unexpected bioenhancer of chlorhexidine in a manner superior to Glucopon® plus chlorhexidine. In particular matters, Glucopon® enhances the activity of the combination CHX plus low concentration of Dowanol® (3%) in a manner superior to CHX plus Glucopon® alone.

In some embodiments of the invention, chlorhexidine is utilized in combination with Dowanol® with or without Glucopon® or Deoxycholate as a disinfectant and has a variety of applications, such as for a skin sanitizer, mouthwash, catheter lock solution, etc. Particular aspects of the invention include chlorhexidine in combination with 50% glycerol as a disinfectant, including for a skin sanitizer, a catheter lock solution, or mouthwash because of the unique activity of this combination as well as the CHX plus Dowanol® against bacteria and biofilm that embed the lumen of the catheter and/or cavity.

One, two, or more of biguanide compounds may be used in the invention, such as chlorhexidine salts, including chlorhexidine (also known as 1,1'-hexamethylene-bis-[5-(4-chlorophenyl)-biguanide]), widely used in the form of its salts (such as the acetate, hydrochloride, and gluconate salts, for example). Other known biguanide-based disinfectants are, for example, the salts of polyhexamethylene biguanide compounds as described in U.S. Pat. No. 4,748,158, which is incorporated by reference herein in its entirety. Numerous antimicrobial biguanide compounds that can be used in the present invention are mentioned in the patent literature, including, for example, European Patent No. 24,031; U.S. Pat. Nos. 2,684,924; 2,990,425; 3,468,898; 4,022,834 and 4,053,636; and German patent Nos. 2,212,259 and 2,627,548, all of which are incorporated by reference herein in their entirety. Additional examples of exemplary antimicrobial biguanide compounds that can be utilized in the present invention include $N^1$-(4-chlorobenzyl)-$N^5$-(2,4-dichlorobenzyl)-biguanide; p-chlorophenyl biguanide; 4-chlorobenzhydryl biguanide; N-3-lauroxypropyl-$N^5$-p-chlorobenzyl biguanide; $N^1$-p-chlorophenyl-$N^5$-lauryl biguanide and the non-toxic addition salts thereof, especially gluconates and acetates.

In specific embodiments, Dowanol® is employed in the invention. The skilled artisan recognizes that this refers to Dipropylene Glycol n-Butyl Ether ($C_4H_9O[CH_2CH(CH_3)O]_2H$). It is a relatively slow-evaporating solvent having properties such as excellent surface tension lowering activity. It has a number of properties that contributed to high latex film quality: it has high polymer plasticizing efficiency; large molecular size and greater polymer mobility contribution; strong partitioning to the polymer phase; relatively slow evaporation rate. It is useful as a cleaning product by itself or when blended with other products.

In certain aspects of the invention, Glucopon® reagents are nonionic surfactants employed in the combination. They combine the formulation ease of typical nonionics with the foam characteristics of anionics. In particular embodiments, Glucopon® reagents are aqueous solutions of alkyl polyglycosides based on natural fatty alcohol (C10-C16). It is a good detergent and in addition to wetting, dispersing, and interfacial tension reduction properties for increased soil removal and emulsification, it also is soluble in concentrated electrolytes and will other hydrotope less soluble ingredients. It is useful in applications where micellar solubilization, emulsification, and detergency are needed. It is soluble and stable in liquid formulations having high levels of builders and electrolytes. It is compatible and can by synergistic with enzymes, optical brightness, and other surfactants, including cationics, in certain embodiments.

In some embodiments, deoxycholate is employed. Sodium deoxycholate is a water-soluble ionic detergent used for cell lysis, membrane protein and lipid isolation, liposome preparation, and other applications. The detergent is used to supplement cell culture media and to prevent nonspecific binding in affinity chromatography. It is an effective reagent for removing lipopolysaccharides from immobilized poly mixin B, allowing reuse of this ligand for additional endotoxin removal.

These antimicrobial solutions may be used to rapidly reduce or eradicate microbial agents from surfaces. For example, as shown in the below examples, it was observed that the triple combination of low concentrations of chlorhexidine+CaEDTA and EtOH completely killed resistant MRSA (as a form of Gram-positive bacteria), resistant *E.*

*coli* (as a form of resistant Gram-negative bacteria), and *C. glabrata* (as a form of resistant fungi), within about 30 seconds of contact time.

In aspects wherein the disinfectant is employed as an environmental disinfectant, the present invention may be provided on the surface of medical supplies, including medical supplies, tools, devices, gauze, sponges, and so forth. The disinfectant may be provided on the surface of a medical device, a pipe, a floor, a table-top, a counter-top, an eating surface, a toy, a high chair, medical equipment, a wheel chair, a phone, a computer, a kitchen sponge, a faucet, light switch cover, a door knob, a door, razor, manicure or pedicure equipment, personal digital assistant, an MP3 player, upholstery, a water fountain, wall, razor, manicure and/or pedicure equipment, personal digital assistant, MP3 player, upholstery, bed linens, toilet, vanity, paper towel dispenser, telephone, store cart, or water fountain, and so forth. The surface may be coated and/or impregnated, for example. In embodiments wherein the disinfectant is employed as an oral or skin sanitizer, it may be provided as a stand-alone skin decontamination composition, such as a hand gel, or it may be provided with other reagents, such as with a soap, including a hand soap, or with a mouthwash, toothpaste, or floss coating. The disinfectant may be employed as an cleanser itself or may be a component of a cleanser having multiple disinfectants.

Therefore, provided are antimicrobial solutions comprising at least one glycol ether and at least one guanidinium compound, and/or at least one chelator, and/or at least one alkylpolyglucoside, and/or glycerol, and/or deoxycholate.

In certain embodiments, one or more non-ionic surfactants may be included in an antimicrobial composition of the present invention. For example, in certain embodiments, there is an antimicrobial composition comprising the glycol ether, dipropylene glycol n-butyl ether, the guanidium compound chlorhexidine; an alkylpolyglucoside such as, for example, capryl glucoside, decyl glucoside, coco-glucoside, or lauryl glucoside; an alcohol (e.g., ethanol or isopropyl alcohol); and/or a chelator (e.g., CaEDTA). Alkylpolyglucosides are commercially available as Glucopon™ products from Cognis (Monheim, Germany), for example.

An "alkylpolyglucoside," "alkyl glucoside" or "alkyl polyglucoside," as used herein, refers to a compound having the following structure:

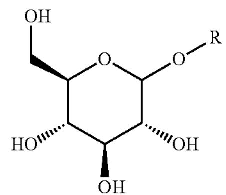

wherein R is an $C_2$-$C_{20}$ alkyl, more preferably a $C_4$-$C_{14}$ alkyl. In certain emodiments, R may be a $C_n$ alkyl, wherein n is 4, 5, 6, 7, 8, 9, 10, 11, 12, 13, 14, 15, 16, 17, 18, 19, or 20. In certain embodiments, R is an unsubstituted alkyl; it is nonetheless anticipated that R may be a substituted alkyl in various embodiments. The alkyl glycoside potentiating agents utilized in accordance with the present invention may be derived using known procedures from fatty alcohols and sugars. Procedures for preparing the alkyl glycoside component of the present invention are well known, as for example illustrated in U.S. Pat. No. 3,598,865. For example, the Fisher process of producing alkyl mono glycosides involves heating glucose and a lower alcohol with an acid catalyst.

One of skill in the art will appreciate that one can use one or more of the antimicrobial agents including one or more antibacterial agents, and/or one or more antifungal agents, and/or one or more antiviral agents, and/or one or more antiseptic agents, and/or combinations thereof.

In some embodiments of the invention, the antimicrobial agent is an antibacterial agent. While any antibacterial agent as described herein may be used in the instant antimicrobial solutions, some non-limiting additional exemplary antibacterial agent(s) that may be used in the antimicrobial composition include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above.

In other embodiments, the antimicrobial agent of the present invention further includes an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109, 496), posaconazole, ravuconazole or flutrimazole; the polyene antifungals such as amphotericin B, liposomal amphoterecin B, natamycin, nystatin and nystatin lipid formulations; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other embodiments of the invention, the antimicrobial agent of the present invention further includes an antiviral agent. Non-limiting examples of antiviral agents include cidofovir, amantadine, rimantadine, acyclovir, gancyclovir, pencyclovir, famciclovir, foscarnet, ribavirin, or valcyclovir. In some embodiments the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial amino acids, peptides, or proteins.

In other embodiments of the invention, the antimicrobial agent of the present invention further comprises an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, silver nitrate, or tetrakis hydroxymethyl phosphonium sulfate (THPS).

In some embodiments of the invention, the antiseptic agent is as set forth in the specification of U.S. Provisional Application Ser. No. 60/261,447, U.S. Provisional Application Ser. No. 60/316,165, and U.S. Non-Provisional patent application Ser. No. 10/044,842, incorporated herein by reference in their entirety. Thus, in some embodiments the antiseptic agent comprises a basic reagent and a dye.

The basic reagent may be a guanidium compound, a biguanide, a bipyridine, a phenoxide antiseptic, an alkyl oxide, an aryl oxide, a thiol, a halide, an aliphatic amine, or an aromatic amine. In some specific aspects, the basic reagent is a guanidium compound. Non-limiting examples of guanidium compounds include chlorhexidine, alexidine, hexamidine. In other specific embodiments, the basic reagent is a bipyridine. One example of a bipyridine is octenidine. In yet other aspects, the basic reagent is a phenoxide antiseptic.

The dye may be a triarylmethane dye, a monoazo dye, a diazo dye, an indigoid dye, a xanthene dye, an anthraquinone dye, a quinoline dye, an FD&C dye. Non-limiting examples of triarylmethane dye include gentian violet, crystal violet, ethyl violet, or brilliant green. Exemplary monoazo dyes include FD&C Yellow No. 5, or FD&C Yellow No. 6. Other non-limiting examples of FD&C dye include Blue No. 1 or Green No. 3. One non-limiting example of diazo dyes is D&C Red No. 17. An example of an indigoid dye is FD&C Blue No. 2. An examples of a xanthene dye is FD&C Red No. 3; of an anthraquinone dye is D&C Green No. 6; and of an quinoline dye is D&C Yellow No. 1.

Other examples of antiseptics that may be used in the antimicrobial solutions of the invention are the phenoxide antiseptics such as clofoctol, chloroxylenol or triclosan. Still other antiseptic agents that may be used to prepare the antimicrobial solutions of the invention are gendine, genlenol, genlosan, or genfoctol.

A wide variety of chelator agents are contemplated as useful in the antimicrobial solutions of the invention. This includes chelators such as EDTA free acid, EDTA 2Na, EDTA 3Na, EDTA 4Na, EDTA 2K, EDTA 2Li, EDTA $2NH_4$, EDTA 3K, Ba(II)-EDTA, Ca(II)-EDTA, Co(II)-EDTACu (II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, Methyl-EDTA, NTA, NTP, NTPO, O-Bistren, TTHA, EGTA, DMSA, deferoxamine, dimercaprol, citrate (such as sodium citrate or zinc citrate, for example), EDDS, sodium metabisulfite, ethylenediaminedisuccinate (EDDS), N-(2-hydroxyethyl)iminodiacetic acid (HEIDA), a combination of bismuth and citrate, penicillamine, succimer or Etidronate. It is contemplated that any chelator that binds barium, calcium, cerium, cobalt, copper, iron, magnesium, manganese, nickel, strontium, or zinc will be acceptable for use in the present invention, in at least certain cases.

Alternatively, one may use at least one anticoagulant such as heparin, hirudin, EGTA, EDTA, urokinase, streptokinase, hydrogen peroxide etc., in the antimicrobial solutions of the invention.

A variety of alcohols are contemplated as useful in the preparation of the instant antimicrobial solution, and include any antimicrobially active alcohol. Non-limiting examples of alcohols include ethanol, methanol, isopropanol, propylene glycol, benzyl alcohol, chlorobutanol, phenylethyl alcohol, and the like. The concentration of the alcohol is preferably in the range of 5%-80% (v/v), more preferably in the range of 10% to 50%, more preferably in the range of 15% to 40%, more preferably in the range of 20% to 30%, with the most preferable being about 25%. Thus, the more preferred concentration of alcohol will include 5%, 6%, 7%, 8%, 9%, 10%, 15%, 20%, 25%, 30%, 35%, 40%, 45%, 50%, 55%, 60%, 65%, 70%, 75%, or 80% (v/v) of the alcohol in the preparation of the instant antimicrobial solutions. This includes the use of intermediate concentrations of alcohol such as 11%, 22.5%, 26% and the like.

One of skill in the art will appreciate that the solutions of the instant invention can comprise various combinations of at least one alcohol, at least one antimicrobial agent, and at least one chelator/anticoagulant. In some specific embodiments, the solution of the invention comprises at least one alcohol and at least one chelator/anticoagulant. In a specific aspect, such an antimicrobial solution comprises ethanol and EDTA or heparin.

The invention also provides methods for reducing microbial organisms from a surface comprising: a) obtaining an antimicrobial solution of the invention as set forth herein; and b) contacting the surface with the antimicrobial solution, whereby said contacting reduces microbial organisms from the surface.

In one embodiment of the method, the contacting is performed for 4 hours or less. In other embodiments of the method, the contacting is performed for 2 hours or less, for 1 hour or less, for 30 minutes or less, or for 15 minutes or less, for 10 minutes or less, for 9 minutes or less, for 8 minutes or less, for 7 minutes or less, for 6 minutes or less, for 5 minutes or less, for 4 minutes or less, for 3 minutes or less, for 2 minutes or less, for 1 minutes or less, for 45 seconds or less, for 30 seconds or less, or for 20 seconds or less.

In another aspect, the method further comprises eradicating microbes from the surface wherein the contacting is performed for about 15 minutes or more.

The methods of the invention can be used to reduce microbial agents from the surface of a medical device such as a catheter, a sponge, a gauze, a bandage, an endotracheal tube, a nephrostomy tube, a biliary stent, an orthopedic device, a prosthetic valve, a medical implant, dental devices or dental implants, cardiac assist devices, vascular grafts, tracheostomy, ventriclulostomy devices, or intrathecal devices. In some aspects, the catheter is an indwelling catheter such as a central venous catheter, a peripheral intravenous catheter, an arterial catheter, a Swan-Ganz catheter, a hemodialysis catheter, an urinary catheter, a peritoneal catheter, an umbilical catheter, a percutaneous nontunneled silicone catheter, a cuffed tunneled central venous catheter or a subcutaneous central venous port.

In other embodiments, the methods of the invention are useful in reducing microbial agents from a surface such as an organic surface or an inorganic surface. An organic surface is exemplified by skin, surgical sutures, mucosal membrane surface, or an epithelial surface. The antimicrobial composition may be swabbed on a human body at a site to be the point of incision. An inorganic surface may be the surface of a pipe or pipeline, a floor, a table-top, a counter-top, hospital equipment, or a wheel chair, etc. Non-limiting examples of a pipe is an oil pipeline, a water pipeline, an ice machine pipe, or a beverage dispensing pipe.

It is contemplated that the antimicrobial solutions of the present invention will find particular usefulness as antimicrobial mouthwash solutions and/or in toothpaste and/or on floss. Such mouthwash solutions are contemplated to be useful both in conjunction with dental procedures and oral sterilization as well as in general dental and oral hygiene applications. Antimicrobial mouthwash is becoming extremely important in the prevention of oral cavity infections as well as aspiration pneumonia. Microbial organisms in the mouth particularly around the teeth, embed themselves in biofilm and the pathogenesis of infection and colonization is similar to that seen in, for example, vascular catheters. In this regard, it is contemplated that one will preferably apply the triple combinations of the present invention, that will include an antimicrobial (possibly antiseptic) with EDTA and low concentration alcohol as a mouthwash or mouth flush solution. In specific embodiments, the antimicrobial composition of the present invention is employed to reduce caries.

In certain embodiments of the invention, the disinfecting compositions include one or more suitable flavorings, for example, methyl salicylate, peppermint oil, sassafras oil and aniseed oil. In certain embodiments, the flavorings are generally used in quantities of from about 0.01 to 2.0% by weight, for example. In specific cases, sweeteners may be used in quantities of from about 0.05 to about 2% by weight, for example.

The invention also provides a kit for disinfecting a surface to reduce microorganisms thereon, wherein the kit comprises components including at least one antimicrobial composition of the present invention contained in a suitable container. The components of the antimicrobial composition may be combined in a single container, or powdered components may be lyophilized, combined and separately compartmentalized, or all of the components may be placed in separate containers. In some embodiments, only one, two, or three of the components of the antimicrobial composition is included as a dried powder. In aspects comprising powdered components, the kit may optionally include a second carrier solution for reconstituting the lyophilized antibiotic agent(s).

Kits in accordance with the present invention may be used to reduce/eliminate microbes on the surface of a medical device, a pipe, a floor, a table-top, a counter-top, an eating surface, a toy, a high chair, medical equipment, a wheel chair, a phone, a computer, a kitchen sponge, a faucet, light switch cover, a door knob, a door, razor, manicure or pedicure equipment, personal digital assistant, an MP3 player, upholstery, a water fountain, wall, razor, manicure or pedicure equipment, personal digital assistant, MP3 player, upholstery, bed linens, or water fountain. It is also contemplated that the kits of the invention will further comprise a means for introducing the kit components into the medical device, the pipe or surface.

In some specific aspects of the invention, a syringe or vial comprising a lyophilized unit dose of a pharmacologically effective amount of one or more of the three components of the flush solutions of the present invention. Such a syringe or vial may further comprises a preselected amount of an ethanol solution such that when the ethanol solution is mixed with the lyophilized unit dose, the desired concentration of the particular agent is obtained.

In other embodiments of the invention, a locking solution for filling and/or flushing a medical indwelling device such as, but not limited to, an implanted catheter is contemplated. The locking solution may comprise at least one antimicrobial composition of the present invention.

In particular embodiments of the present invention, the antimicrobial agent is effective against Gram-positive and/or Gram-negative bacteria. In specific embodiments, the disinfectant is useful against pathogenic bacteria. In specific embodiments, the antimicrobial agent is effective against one or more bacteria selected from the group consisting of the following phyla: 1) Aquificae; 2) Xenobacteria; 3) Fibrobacter; 4) Bacteroids; 5) Firmicutes; 6) Planctomycetes; 7) Chrysogenetic; 8) Cyanobacteria; 9) Thermomicrobia; 10) Chlorobia; 11) Proteobacteria; 12) Spirochaetes; 13) Flavobacteria; 14) Fusobacteria; and 15) Verrucomicrobia. In specific cases, the disinfectants of the present invention are useful against Gram positive cocci; Gram negative cocci; Gram positive bacilli; Gram negative bacilli, Spirochaetes, *Rickettsia*, and *Mycoplasma*. In certain embodiments, the present invention is useful against one or more bacteria that are resistant to one or more antibacterial agents, such as one or more antibiotics.

In certain cases, the disinfectants are useful against *Staphylococcus, Streptococcus, Corynebacterium, Listeria, Bacillus, Clostridium, Neisseria, Enterobacteria, E. coli, Salmonella, Shigella, Campylobacter, Chlamydia, Borrelia, Francisella, Leptospira, Treponema, Proteus, Yersinia pestis, Vibrio, Helicobacter, Haemophila, Bordetella, Brucella*, and *Bacteriodes*. In particular cases, the disinfectants are useful against *Staphylococcus aureus, Listeria monocytogenes, Clostridium botulinum, Legionella pneumophila, E. coli, Salmonella enterica, Neisseria meningitides, Yersinia pestis, Mycobacterium tuberculosis, Vibrio cholera*, Group A hemolytic streptocoei, *Diplococcus pneumonia, Moraxella catarrhalis, Neisseria gonorrhoeae, C. jeikeium, Mycobacterium avium complex, M. kansasii, M. leprae, M. tuberculosis, Nocardia* sp, *Acinetobacter calcoaceticus, Flavobacterium meningosepticum, Pseudomonas aeruginosa, P. alcaligenes*, other *Pseudomonas* sp, *Stenotrophomonas maltophilia, Brucella, Bordetella, Francisella, Legionella* spp, *Leptospira* sp, *Bacteroides fragilis*, other *Bacteroides* sp, *Fusobacterium* sp, *Prevotella* sp, *Veillonella* sp, *Peptococcus niger, Peptostreptococcus* sp, *Actinomyces, Bifidobacterium, Eubacterium*, and *Propionibacterium* spp, *Clostridium botulinum, C. perfringens, C. tetani*, other *Clostridium* sp, *Staphylococcus aureus* (coagulase-positive), *S. epidermidis* (coagulase-negative), other coagulase-negative staphylococci, *Enterococcus faecalis, E. faecium, Streptococcus agalactiae* (group B *streptococcus*), *S. bovis, S. pneumoniae, S. pyogenes* (group A *streptococcus*), viridans group streptococci (*S. mutans, S. mitis, S. salivarius, S. sanguis*), *S. anginosus* group (*S. anginosus, S. milleri, S. constellatus*), *Gemella morbillorum. Bacillus anthracis, Erysipelothrix rhusiopathiae, Gardnerella vaginalis* (gram-variable), Enterobacteriaceae (*Citrobacter* sp, *Enterobacter aerogenes, Escherichia coli, Klebsiella* sp, *Morganella morganii, Proteus* sp, *Providencia rettgeri, Salmonella typhi*, other *Salmonella* sp, *Serratia marcescens, Shigella* sp, *Yersinia enterocolitica, Y. pestis*), *Aeromonas hydrophila, Chromobacterium violaceum, Pasturella multocida, Plesiomonas shigelloides, Actinobacillus actinomycetemcomitans, Bartonella bacilliformis, B. henselae, B. quintana, Eikenella corrodens, Haemophilus influenzae*, other *Haemophilus* sp,

*Mycoplasma pneumonia, Borrelia burgdorferi, Treponema pallidum Campylobacter jejuni, Helicobacter pylori, Vibrio cholerae, V. vulnificus, Chlamydia trachomatis, Chlamydophila pneumoniae, C. psittaci, Coxiella burnetii, Rickettsia prowazekii, R. rickettsii, R. typhi, R. tsutsugamushi, R. africae, R. akari, Ehrlichia chaffeensis*, and *Anaplasma phagocytophilum.*

In particular embodiments of the present invention, the antimicrobial agent is effective against one or more viruses, including one or more pathogenic viruses. In specific embodiments, the antimicrobial agent is effective against one or more viruses selected from the group consisting of Adenoviridae, Picornaviridae, Herpesviridae, Hepadnaviridae, Flaviviridae, Retroviridae, Orthomyxoviridae, Parvoviridae, Paramyxoviridae, Papovaviridae, Polyomavirus, Rhabdoviridae, and Togaviridae. Particular viruses include, for example, HIV, Adenovirus Influenza A, Rabies virus, Hepadnavirus, Varicella-zoster virus, Herpes simplex virus (types 1 and 2), Ebolavirus, Epstein Barr virus, Varicella-zoster virus, pox virus (including smallpox, copox, or monkey pox), human cytomegalovirus, poliovirus, coxsackievirus, Rubeola virus (paramyxovirus), Rubella virus, Variola virus, Avian flu virus (Influenza A virus), hepatitis A, B, and C viruses, parainfluenza, mumps virus, measles virus, respiratory syncitial virus, West Nile virus, Dengue fever virus, yellow fever virus, foot and mouth disease virus, and severe acute respiratory syndrome (SARS) coronavirus.

In particular embodiments of the present invention, the antimicrobial agent is effective against one or more fungi, including one or more pathogenic fungi. In specific embodiments, the antimicrobial agent is effective against one or more fungi selected from the group consisting of *Histoplasma, Aspergillus* and other common household molds, *Candida, Cryptococcus, Stachybotrys, Zygomycosis, Fusarium, Blastomycosis, Coccidioides, Scedosporium*, and *Pneumocystis.*

In some cases, the antimicrobial composition is employed against prions.

The present invention may be employed as a disinfectant for the benefit of a mammal, including a human, dog, cat, cow, horse, pig, sheep, goat, and so forth. In certain embodiments of the invention, the antimicrobial composition is applied to the teets of a cow prior to milking or to chicken eggs.

In one embodiment of the invention, there is an antimicrobial composition comprising at least one biguanide and at least one glycol ether. In a specific embodiment, the method further comprises at least one of the following agents: a) an alkylpolyglucoside, wherein the alkylpolyglucoside has the structure:

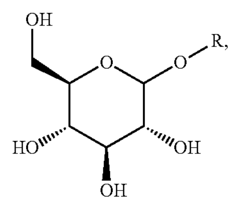

wherein R is an C2-C20 alkyl (such as C4-C14 alkyl), b) deoxycholate, c) at least one chelator, d) at least one alcohol, and/or e) glycerol. In specific embodiments the anticmicrobial composition comprises a biguanide, a glycol ether, and an alkylpolyglucoside. In certain embodiments, the composition comprises a biguanide, a alkylpolyglucoside, a chelator, and an alcohol. In particular aspects, the composition comprises a biguanide, glycol ether and deoxycholate. In certain cases, the composition comprises a biguanide, a glycol ether, an alkylpolyglucoside, and deoxycholate.

In particular embodiments, the alkylpolyglucoside is selected from the group consisting of capryl glucoside, decyl glucoside, coco-glucoside, and lauryl glucoside. In certain embodiments, the guanidium compound is selected from the group consisting of chlorhexidine, alexidine, hexamidine. In some cases, the glycol ether is dipropylene glycol n-butyl ether. In particular embodiments, the chelator is selected from the group of chelators consisting of EDTA free acid, EDTA 2Na, EDTA 3Na, EDTA 4Na, EDTA 2K, EDTA 2Li, EDTA 2NH4, EDTA 3K, Ba(II)-EDTA, Ca(II)-EDTA, Co(II)-EDTACu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, Methyl-EDTA, NTA, NTP, NTPO, O-Bistren, TTHA, EGTA, DMSA, deferoxamine, dimercaprol, citrate, EDDS, sodium metabisulfite, zinc citrate, a combination of bismuth and citrate, penicillamine, succimer and Etidronate. In some aspects, the alcohol is selected from the group consisting of ethanol and isopropyl alcohol.

Certain ranges of the components of the antimicrobial composition are encompassed in the invention. In some cases, the concentration of guanidinium compound is about 0.01%-6%; the concentration of dipropylene glycol n-butyl ether is about 1%-12%; the concentration of alkylpolyglucoside is about 0.1%-10%; the concentration of chelator is about 0.1%-20%; and/or the concentration of alcohol is in the range of about 1%-80%. In some cases, the concentration of alcohol is in the range of about 15-30%. In particular aspects, the concentration of alcohol is less than about 10% and may be from about 0.25% to about 5%, in certain embodiments. In particular embodiments, the alcohol is ethanol, and wherein the chelator is EDTA or CaEDTA.

In another embodiment of the invention, there is a method for reducing microbial organisms from a surface or preventing growth of microbial organisms comprising contacting the surface with an antimicrobial composition of the invention. The contact of surfaces may be further defined as impregnating at least part of the surface with the antimicrobial composition. Contact can be for any duration, although in specific embodiments the contacting is performed for 1 hour or less, such as for 15 minutes or less, including for about from 10 seconds, 15, second, 20 seconds, 25 seconds, 30 seconds, 45 seconds, 1 minute, 1.5 minutes, 2 minutes 2.5 minutes, 3 minutes, 3.5 minutes, 4 minutes, 4.5 minutes, to about 5 minutes.

Surfaces contacted by the antimicrobial composition may be of any kind that harbor one or more pathogenic entities. The surface may be the surface of medical equipment, such as a bed, computer, glove, clothing, ice machine, forceps, scalpel, syringe, or clamp. The surface may be a medical device, such as a patch, sponge, gauze, bandage, a catheter, an endotracheal tube, a nephrostomy tube, a chest tube, a stent, an orthopedic device, a prosthetic valve, a medical implant, dental devices or dental implants, cardiac assist devices, vascular grafts, tracheostomy, ventriclulostomy devices, or intrathecal devices. When the surface is a stent, it may be of any kind, but in specific cases the stent is a biliary stent, coronary, urethral/prostatic, urinary, vascular, CHD, esophageal, duodenal, colonic, or pancreatic stent. When the surface is a catheter, it may be any kind of catheter, although in specific aspects the catheter is an indwelling catheter, such as a central venous catheter, a peripheral intravenous catheter, an arterial catheter, a Swan-Ganz catheter, a hemodialysis catheter, an urinary catheter, a peritoneal catheter, an umbilical catheter, a percutaneous nontunneled silicone catheter, a cuffed tunneled central venous catheter or a subcutaneous central venous port.

In specific embodiments a surface in a medical environment is contacted such as on drapes, a mattress, a pillow, a pillowcase, a sheet, laundry, wall, cabinet, drain, sink, toilet, bathtub, shower, countertop, waste receptacle, medical device, or medical equipment, for example.

In some aspects the surface is an organic surface, such as skin, surgical suture, mucosal membrane surface, or epithelial surface. The organic surface may be an oral cavity or other mucosal surface. In aspects wherein the surface is an inorganic surface, such as the surface of a pipe, a floor, a table-top, a counter-top, hospital equipment, a toy, an eating surface, high chair, medical equipment, medical device, phone, computer, kitchen sponge, faucet, light switch cover, doorknob, door, wall, razor, manicure or pedicure equipment, personal digital assistant, MP3 player, upholstery, bed linens, water fountain, or a wheel chair, for example. In particular cases, the inorganic surface is plastic, glass, marble, ceramic, vinyl, stone, or metal.

When the surface is a pipe, the pipe may be of any kind, but in specific cases the pipe is an oil pipeline, gas pipeline, a water pipeline, an ice machine pipe, or a beverage-dispensing pipe, for example.

Contacting the surface may include contact of a hard surface or a soft surface or both. In certain embodiments, the surface is in or on a gym, healthcare facility, camp, restroom, restaurant, school, daycare, cruise ship, household, mall, elevator, office building, kitchen, bedroom, hotel, motel, shower, airport, airplane, bus, car, train, boat, bus station, train station, marina, park, changing table, or stroller.

In particular embodiments, there is a kit for disinfecting a surface to reduce microorganisms thereon, wherein the kit comprises an antimicrobial composition of any the invention, wherein the biguanide and the glycol ether are contained in separate containers or a single container. In specific aspects, the kit comprises at least one alkylpolyglucoside, at least one chelator, at least one alchohol, deoxycholate, and/or glycerol. In one exemplary case, the alcohol, the chelator, the deoxycholate, the glycerol and/or the alkylpolyglucoside are each contained in separate containers. In specific embodiments, at least two of the glycol ether, the guanidinium compound, the chelator, deoxychoalte, glycerol, and the alkylpolyglucoside are contained in a suitable container. In some embodiments, at least three of the glycol ether, the biguanide, the chelator, deoxycholate, glycerol, and the alkylpolyglucoside are contained in a suitable container means. The chelator is lyophilized or otherwise constituted as a dried powder, in certain aspects. The kit may further comprise a second carrier solution for reconstituting the dried chelator. The kit may comprise a lyophilized unit dose of a pharmacologically effective amount of the guanidium compound and the chelator to be mixed in an ethanol solution.

In some embodiments of the invention, the surface is the surface of a medical device, a pipe, a floor, a table-top, a counter-top, an eating surface, a toy, a high chair, medical equipment, a wheel chair, a phone, a computer, a kitchen sponge, a faucet, light switch cover, a door knob, a door, razor, manicure or pedicure equipment, personal digital assistant, an MP3 player, upholstery, a water fountain, wall, razor, manicure or pedicure equipment, personal digital assistant, MP3 player, upholstery, bed linens, or water fountain. The medical device may be a catheter. The kit may further comprise a means for introducing the kit components into the medical device or the pipe.

In one embodiment of the invention, there is a syringe, comprising a unit dose of a pharmacologically effective amount of the solution of an antimicrobial composition of the invention.

In a certain embodiment, there is a vial, comprising a lyophilized unit dose of a pharmacologically effective amount of the solution of an antimicrobial composition of the invention.

In certain aspects, there is an antimicrobial composition comprising at least one biguanide and one of the following: a) deoxycholate; or b) a combination of at least one chelator, at least one alcohol, and at least one alkylpolyglucoside.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
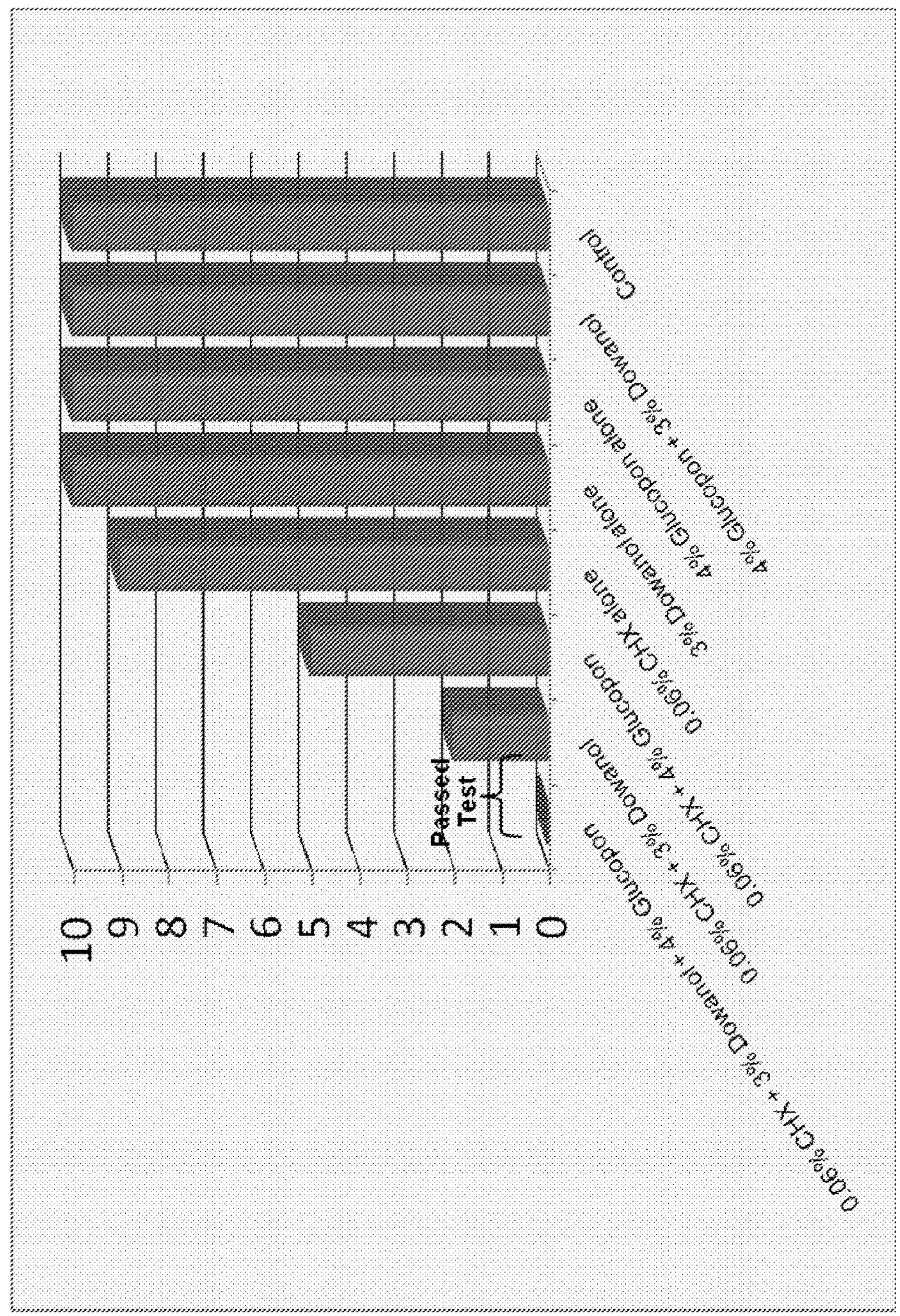
FIG. 1 compares particular exemplary combinations of CHX+Glucopon® or CHX+Dowanol® to other components or combinations, with exposures of one minute.

As used herein in the specification, “a” or “an” may mean one or more. As used herein in the claim(s), when used in conjunction with the word “comprising”, the words “a” or “an” may mean one or more than one. As used herein “another” may mean at least a second or more. Some embodiments of the invention may consist of or consist essentially of one or more elements, method steps, and/or methods of the invention. It is contemplated that any method or composition described herein can be implemented with respect to any other method or composition described herein.

As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria.

As used herein, the term "antifungal agent" is defined as a compound having either a fungicidal or fungistatic effect upon fungi contacted by the compound. As used herein, the term "fungicidal" is defined to mean having a destructive killing action upon fungi. As used herein, the term "fungistatic" is defined to mean having an inhibiting action upon the growth of fungi.

An "antimicrobial agent" is defined herein as an agent that has antibiotic properties against bacteria, fungi, viruses and other pathogens and includes antibacterial agents, antifungal agents, antiviral agents and antiseptic agents. These components are present in effective amounts to reduce and/or prevent microbial growth.

As used herein, the term "antiviral agent" is defined as a compound that can either kill viral agents or one that stops the replication of viruses upon contact by the compound.

As used herein, the term biguanide (which may be called diguanide or 2-carbamimidoylguanidine or guanylguanidine) refers to molecules based on the following exemplary structure:

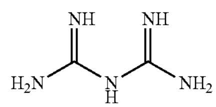

As used herein, the term "bioenhancer" is defined as an agent that does not achieve complete or near complete kill on its own but complements the antimicrobial activity of another such that the combination achieves near or complete kill. In certain cases, the term "near kill" refers to a substantial reduction in microbial growth that either equals to or exceeds 99.9% kill.

The phrase "a chelator" denotes one or more chelators. As used herein, the term "chelator" is defined as a molecule comprising nonmetal atoms, two or more of which atoms are capable of linking or binding with a metal ion to form a heterocyclic ring including the metal ion.

For the purposes of this disclosure, the phrase "effective amount" or "therapeutically effective amount" is defined as a dosage sufficient to induce a microbicidal or microbistatic effect upon the microbes contacted by the composition on a surface.

As used herein, the term "guanidium compound" refers to the cation derived from guanidine (guanidine is a strong base $HN{=}C(NH_2)_2$ obtained by the oxidation of guanine); the compound has the following exemplary structure:

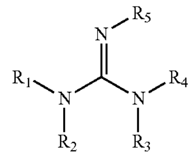

As used herein the terms "contact", "contacted", and "contacting", or "exposed" and "exposure" are used to describe the process by which any of the compositions disclosed in the present invention, comes in direct juxtaposition with the surface of a medical device or any other surface from which microbial growth is to be reduced or eradicated.

Microorganisms that attach themselves to inert surfaces, such as medical devices including, vascular catheters, endotracheal tubes, Foley catheters, biliary stents, nephrostomy tubes, prosthetic valves, ventriculostomy or epidural catheters, or fluid pipelines, such as oil pipelines or water pipelines, produce a layer made of exopolysaccharide called microbial biofilm. These organisms embed themselves in this layer. This biofilm layer ultimately becomes the protective environment that shields these organisms on the inert surface from the antimicrobial activity of various antibiotics or antiseptics. In U.S. Pat. Nos. 5,362,754 and 5,688,516, incorporated herein by reference in their entirety, the present inventor demonstrated that a combination of one or more antimicrobial agent with one or more chelator and/or anticoagulant (such as EDTA or heparin) reduces or eradicates these antibiotic-resistant biofilm embedded microorganisms if the antimicrobial and chelator combination is allowed to dwell on the surface for at least 4 hours. However, in both clinical and environmental situations, it is typically not feasible to allow a 4 hour dwell time for the chelator and antimicrobial agent to reduce or eradicate the microbes. For example, it is not possible to interrupt the therapy of critically ill patients receiving continuous infusion therapy through a vascular catheter for 4 hours. It is also not possible to interrupt an environmental situation involving fluid pipelines for 4 hours to allow for such a prolonged dwell time of antimicrobial/chelator solution.

The present invention regards a combination of antimicrobials that has at least two active components including (1) a guanidium compound, such as chlorhexidine, for example; (2) a glycol ether, such as dipropylene glycol n-butyl ether; and, optionally (3) a bioenhancer, for example, a Glucopon® surfactant or deoxycholate, and/or EDTA, and/or alcohol, and/or glycerol. This combination is highly safe, effective and, unlike the currently used disinfectants, fulfills one or more criteria that are useful for a universal ideal optimal disinfectant: broad-spectrum activity against various pathogens; no potential health risk to personnel or users (as is the case with chlorine bleach solutions, phenolic based solutions, and quarternary ammonium chlorides; no hazardous properties (such as being flammable, volatile, corrosive, or toxic, for example); stable at a wide range of pH; active in the presence of contaminants, including soil and water; active during a rapid unit of time (such as a minute, for example); minimal requirement for disposal with minimal biohazard concerns; and/or cost-effective.

The present invention utilizes low concentrations of very safe disinfectants, such as combinations including chlorhexidine, Glucopon®, Dowanol®, and/or deoxycholate, which demonstrate unexpected synergy with a high efficacy and an exceptional degree of safety to the end user and the environment.

A. ANTIMICROBIAL COMPOSITIONS

An aspect of the present invention is based on the observation that solutions containing a glycol ether and a guanidinium compound, optionally with a chelator, an alkylpolyglucoside, an alcohol, and/or glycerol, exhibit surprising and unexpected increases in antimicrobial properties. In other embodiments, solutions containing combinations of two or three or more of an alcohol, a guanidinium compound, a chelator, deoxycholate and an alkylpolyglucoside may be used to achieve antimicrobial effects. In certain embodiments, the antimicrobial solutions may be used with minimal or no toxicity to the user or recipient, such as a subject whose skin is cleaned prior to a surgical procedure. Antimicrobial compositions described herein may be used for the rapid reduction or eradication of microorganisms embedded in a biofilm on a surface comprising contacting or exposing the surface to a flush solution of the invention. Thus, the invention provides methods for reducing or eradicating microbes from the surfaces of medical devices, including indwelling medical devices, as well as other surfaces, pipelines and the like.

In certain aspects, the compositions and the methods of the present invention have an unexpected and surprising efficacy not provided by compositions that comprise only alcohol solutions, or at least certain compositions that comprise combinations of antimicrobials with chelators/anticoagulants.

1. Medical Applications

Medical devices, such as vascular catheters, have improved the quality of medical care. However, infections resulting from the colonization of organisms embedded in biofilm are the most frequent complication associated with the use of these and other indwelling and/or prosthetic devices. In fact, infections are the most serious complications associated with indwelling central venous catheters (CVCs) (Maki et al., 1998). It is estimated that more than 200,000 catheter-related bloodstream infections (CRBSI) occur annually in the United States alone (Kluger et al., 1999). *Staphylococcus epidermidis, Staphylococcus aureus* and *Candida* species are the leading organisms causing CRBSI (Maki et al., 1998; Raad et al., 2002).

Because intralumenal colonization is the major source for the migration of organisms leading to bloodstream infections in long-term silicone catheters (Raad et al., 1993), recent guidelines by the CDC and Infectious Diseases Society of America have proposed the use of intralumenal antimicrobial lock solutions for the prevention and treatment of CRBSI (Mermel et al., 2001; Centers for Disease Control and Prevention, 2002). Most long-term CVCs are typically flushed with heparin. An antimicrobial/anticoagulant combination consisting of vancomycin/heparin with and without ciprofloxacin was shown to reduce the risk of catheter-related bacteremia caused by gram-positive organisms (Carratala et al., 1999; Henrickson et al., 2002; Schwartz et al., 1990). However, with the rise of incidences of infection by vancomycin resistant gram-positive bacteria, concerns have been raised over the use of vancomycin flush solutions and their potential for increasing the risk of vancomycin resistance (Spafford et al., 1994).

Recently the present inventor demonstrated that a flush solution comprising minocycline and EDTA (M-EDTA) is highly efficacious in preventing catheter-related colonization, bacteremia and endocarditis in rabbits (Raad et al., 2002). When compared to a heparin flush solution, M-EDTA was found to decrease the risk of catheter-related colonization and infection in hemodialysis patients as well as pediatric cancer patients (Bleyer et al., 2000; Chatzinikolaou et al., 2002). EDTA has an equivalent anticoagulant activity to heparin (Reardon et al., 1991). An anticoagulant in flush solutions is necessary to prevent the thrombotic occlusion of the catheter lumen.

Although M-EDTA has been found to be efficacious in preventing CRBSI, this solution may not be applicable given some of the limitations of the real world of clinical practice. In the animal and clinical studies, the M-EDTA lock solution was required to be exposed to the surface of the indwelling medical device, such as the lumen of catheters, for at least 4 hours. In vitro studies have also shown that M-EDTA requires at least 4 hours of dwell time to eradicate organisms that colonize the lumen of the catheter (see U.S. Pat. No. 5,362,754 and U.S. Pat. No. 5,688,516). Providing a four hour exposure time to reduce microbes using the M-EDTA solution is usually not possible in critically ill patients who require continuous infusion therapy, including parenteral nutrition.

One of the applications of the antimicrobial flush solutions of the invention is to reduce or eradicate microbes from the surfaces of medical devices, especially indwelling medical devices such as catheters, endotracheal tubes, nephrostomy tubea, biliary stents, orthopedic devices, prosthetic devices, and/or medical implants, for example.

There are at least 5 million central venous catheters inserted annually in the United States, 1.5 million of which are long-term catheters that remain in place for an average of 100 days, and at least 3.5 million short-term catheters that remain for an average of 7 days. All of these venous catheters are flushed with heparin on a daily basis. It is estimated that at least 150-175 million catheter flushes occur annually in the United States alone. Heparin has good anticoagulant activity and, hence, prevents thrombotic occlusions. However, heparin has no antimicrobial activity and, in fact, given the alkaline media that heparin creates, it has been shown to be a promoter of microbial colonization of catheter surfaces. Irrespective of whether heparin is used, almost 90%-100% of indwelling vascular catheters end up being colonized with organisms embedded in biofilm on the surface of these devices, particularly at the lumenal surface. Hence, the most serious and frequent complication of vascular catheters is infection, whereby as fluid is flushed through the lumen of the catheter, microorganisms migrate into the bloodstream and cause catheter-related bloodstream infections. Indwelling central venous catheters are associated with around 5%-8% frequency of catheter-related bloodstream infection, which in turn is associated with an attributable mortality of 25% in critically ill patients. Such an event is also associated with high morbidity and a cost per episode of an average of $30,000.

EDTA is a well-known chelator of iron and calcium, as well as an active anticoagulant used in blood collection tubes. EDTA has been shown to have equivalent anticoagulant activity to heparin. In addition, EDTA has antibiofilm activity and enhances the antimicrobial activity of other antimicrobial agents, such as minocycline. However, for a combination of an antmicrobial with a chelator (such as minocycline-EDTA) to eradicate organisms embedded in biofilm, contacting the surface for at least 4-hour with this combination is required. This is demonstrated in U.S. Pat. No. 5,362,754 and in U.S. Pat. No. 5,688,516. This prolonged period of contacting or dwell time is not possible in the highest risk patient population (i.e., in patients receiving total parental nutrition or critically ill patients, for example), as these patients require a continuous, often uninterrupted, infusion through the catheter. In order to allow for a rapid reduction or eradication of microorganisms, an improvement has been developed in the present invention wherein the antimicrobial(s) is highly effective in a minimal period of time.

In certain embodiments, indwelling medical devices such as catheters are flushed with an antimicrobial solution as described herein, resulting in broad-spectrum reduction or eradication of microbial organisms embedded in biofilm.

Some examples of indwelling medical devices that may be treated with the solutions of the present invention include abdominal cavity drainage bags, connectors and tubing used by colostomy patients, vascular shunts, orthopedic, intraocular, or penile prosthesis devices, for example. Angioplasty devices, heart valves and cardiac pacemakers also are included within the present invention, in certain embodiments. Catheters such as urinary, venous, arterial, and peritoneal catheters may be treated with the flush solutions of the invention, for example. In addition, tracheotomy devices, shunts, surgical sutures, and other medical devices or prosthesis can be treated, in particular aspects.

Furthermore, the medical devices that are amenable to coatings of the compositions of the invention generally have surfaces composed of thermoplastic or polymeric materials, such as polyethylene, Dacron, nylon, polyesters, polytetrafluoroethylene, polyurethane, latex, silicone elastomers and the like. Devices with metallic surfaces are also amenable to coatings with the antibiotic combinations. Such devices are exemplified by bone and joint prosthesis. It is also contemplated that the solutions of the invention will be used to disinfect organic surfaces such as skin as well as mucosal surfaces.

An antimicrobial locking solution of the present invention may comprise at least at least one glycol ether, at least one alcohol, at least one guanidinium compound, at least one chelator, and/or at least one alkylpolyglucoside. For catheter applications, various antimicrobial substances as disclosed herein and that are well known to one of ordinary skill in the art may be combined with the locking solution in order to inhibit infection. The antimicrobial locking solution of the present invention may be use for filling or flushing a medical device such as an indwelling device such as an implanted catheter. Other medical devices that are contemplated for use in the present invention are disclosed herein.

2. Environmental Applications

Other than reduction/eradication of microbes in medical devices, the flush solutions of the present invention are also useful in the eradication of the surfaces of other surfaces that microbes can grow on such as pipes, pipelines etc. Fluid pipelines, such as oil and water pipelines, are often obstructed by lumenal biofilm that is produced by microorganisms that colonize the internal surface of these pipelines. Often these pipelines are flushed with antimicrobial agents. However, antimicrobial and antiseptic agents have little activity against organisms embedded in biofilm. Tons of antibiotics, such as gentamicin, are often used to flush the lumen of oil pipelines, to no avail. The present invention provides new and effective compositions and methods for the eradication of organisms, as well as biofilm embedding the lumen of pipelines (oil, water), as well as other devices, such as ice machines. These pipelines or machines can be flushed or rinsed with the compositions of the invention that comprise at least one antimicrobial compositions of the invention. Flushing the pipelines, machines or tubes with the compositions of the invention provide rapid reduction and/or eradication of the biofilm and the organisms in biofilm thereby preventing any obstruction or contamination of the water, oil or the ice machines in certain environmental settings.

B. ANTIMICROBIAL AGENTS AND MICROBES

The present compositions are contemplated to have one or more antimicrobial agents. "Antimicrobial agents" are defined herein as antibacterial agents, antifungal agents, antiviral agents and/or antiseptic agents.

While the invention is not limited to any particular antimicrobial agent some exemplary classes and examples of antibacterial agents, antifungal agents, antiviral agents as well as antiseptic agents are described elsewhere herein. Of course one of skill in the art will appreciate that any combination as well as agents from the different types and classes of the antimicrobial agents can be combined to prepare the solutions of the invention.

Some non-limiting exemplary bacterial and fungal microbes that can be reduced or eradicated by the compositions and methods of the invention include *Staphyloccous* species such as *Staphylococcus epidermidis, Staphylococcus aureus; Aspergllus* species, such as *Aspergillus flavus, Aspergillus terreus; Fusarium oxysporum, Candida* species, such as *Candida krusei, Candida parapsilosis, Candida tropicalis, Candida albicans* and *Candida glabrata*. In addition, viruses can also be reduced or eradicated.

C. ALKYLPOLYGLUCOSIDE SURFACTANTS

An aspect of the present invention is based upon the observation that inclusion of an alkylpolyglucoside in an antimicrobial solution can significantly increase the antimicrobial properties of the solution. Alkylpolyglucosides are a class of non-ionic surfactants that may be used in homes and/or personal care products, such as baby shampoos, facial cleaners, wipes, laundry detergents, or hard surface cleaners. Various alkylpolyglucosides may be made from sugar and a vegetable oil such as coconut oil. Alkylpolyglucosides are typically very mild on human skin and exhibit low ecotoxicity.

In certain embodiments, one or more non-ionic surfactants may be included in an antimicrobial composition of the present invention. For example, in certain embodiments, an antimicrobial composition comprising chlorhexidine, a glycol ether, an alcohol (e.g., ethanol or isopropyl alcohol), and/or a chelator (e.g., CaEDTA) may also comprise an alkylpolyglucoside such as, for example, capryl glucoside, decyl glucoside, coco-glucoside, or lauryl glucoside. Alkylpolyglucosides are commercially available as Glucopon® products from Cognis (Monheim, Germany).

In certain embodiments 3% CaEDTA may be slowly dissolved in an alkylpolyglucoside and then an alcohol (e.g., ethanol) may be added to achieve a concentration range, e.g., below 10% total alcohol, and then chlorhexidine may be added to achieve a concentration, e.g., below about 1.5%.

An "alkylpolyglucoside," "alkyl glucoside" or "alkyl polyglucoside," as used herein, refers to a compound having the following structure:

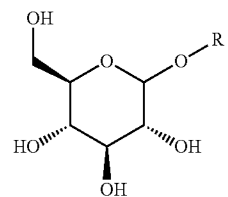

wherein R is an $C_2$-$C_{20}$ alkyl, more preferably a $C_4$-$C_{14}$ alkyl. In certain embodiments, R may be a $C_n$ alkyl, wherein n is 4, 5, 6, 7, 8, 9, 10, 11, 12, 13, 14, 15, 16, 17, 18, 19, or 20. In certain preferred embodiments, R is an unsubstituted alkyl; it is nonetheless considered that R may be a substituted alkyl in various embodiments.

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —$CH_2OH$, —$CH_2Cl$, —$CH_2Br$, —$CH_2SH$, —$CF_3$, —$CH_2CN$, —$CH_2C(O)H$, —$CH_2C(O)OH$, —$CH_2C(O)OCH_3$, —$CH_2C(O)NH_2$, —$CH_2C(O)NHCH_3$, —$CH_2C(O)CH_3$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, —$CH_2CF_3$, —$CH_2CH_2OC(O)CH_3$, —$CH_2CH_2NHCO_2C(CH_3)_3$, and —$CH_2Si(CH_3)_3$.

Non-limiting examples of alkylpolyglucosides include: capryl glucoside:

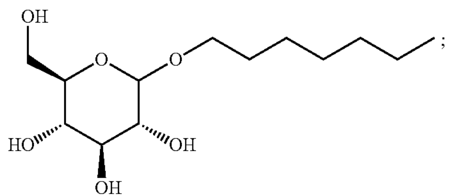 [SMILES: CCCCCCCOC1O[C@H](CO)[C@@H](O)[C@H](O)[C@H]1O]

decyl glucoside:

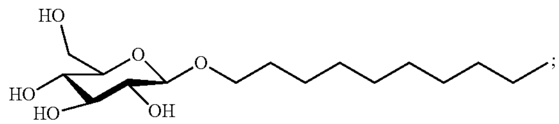

coco-glucoside; octyl glucoside, such as β-D-octyl glucoside:

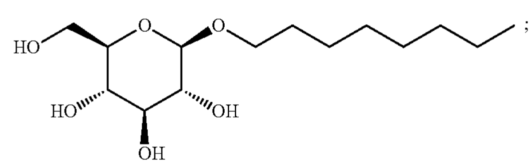 [SMILES: CCCCCCCCO[C@@H]1O[C@H](CO)[C@@H](O)[C@H](O)[C@H]1O]

and lauryl glucoside:

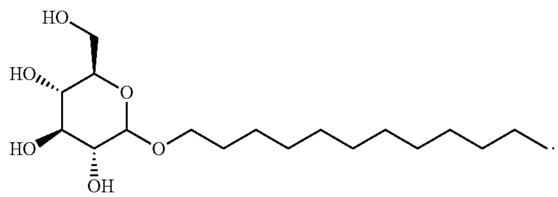 [SMILES: CCCCCCCCCCCCOC1O[C@H](CO)[C@@H](O)[C@H](O)[C@H]1O]

Non-limiting examples of surfactants that may be included in an antimicrobial composition, as described herein, are provided below in Table 1. Technical data for the below surfactants is known in the art and available, e.g., from Chemidex (see Chemidex website).

TABLE 1

| Surfactants | | |
|---|---|---|
| Provider | Brand Name | Description |
| Cognis - Care Chemicals | DEHYPON ® 3697 GRAM | DEHYPON ® 3697 GRAM is a low-foaming fatty alcohol polyglycolether surfactant. The product is supplied in a granual form and is suitable for use as a rinse aid and surfactant for multifunctional automatic dish wash products. |
| Cognis - Care Chemicals | DEHYPON ® 3697 GRAM | DEHYPON ® 3697 GRAM is a low-foaming fatty alcohol polyglycolether surfactant. The product is supplied in a granual form and is suitable for use as a rinse aid and surfactant for multifunctional automatic dish wash products. |
| Cognis - Care Chemicals | DEHYPON ® E 124-96 | DEHYPON ® E124-96 is a low-foaming fatty alcohol polyglycolether surfactant. The product is supplied as a liquid and is suitable for use as a rinse aid and surfactant for multifunctional automatic dish wash products. |
| Cognis - Care Chemicals | DEHYPON ® E 124-96 | DEHYPON ® E124-96 is a low-foaming fatty alcohol polyglycolether surfactant. The product is supplied as a liquid and is suitable for use as a rinse aid and surfactant for multifunctional automatic dish wash products. |
| Cognis - Care Chemicals | DEHYPON ® LS 36 | DEHYPON ® LS 36 is a low-foaming fatty alcohol C12-C14 3EO/6PO derivative surfactant suitable for formulation for technical and institutional areas. Other applications involve all-purpose cleaners, floor cleaners and hard surface cleaners. |
| Cognis - Care Chemicals | DEHYPON ® LS 54 | DEHYPON ® LS 54 is a low-foaming fatty alcohol C12-C14 5EO/4PO derivative surfactant with excellent environmental properties. |
| Cognis - Care Chemicals | DEHYPON ® LT 054 | DEHYPON ® LT 054 is low foaming surfactant with good wetting properties. It has a good stability with caustic solutions and acids as well as oxidizing and reducing substances. It is particulary suited for powder formulations based on caustic soda. |
| Cognis - Care Chemicals | DEHYPON ® LT 054 | "DEHYPON ® LT 054 is miscible with anionic, cationic and nonionic surfactant. Water hardness does not affect the application of DEHYPON ® LT 054. It has good alkalinity stability and particularly suitable for powder formulation based |

TABLE 1-continued

| Surfactants | | |
|---|---|---|
| Provider | Brand Name | Description |
| | | on caustic soda in which a decrease in defoaming effect is not witnessed for after a long storage. it is recommended where low foaming is needed at room temperature. |
| Cognis - Care Chemicals | DEHYPON ® LT 104 | DEHYPON ® LT 104 is low foaming surfactant with good wetting properties. It has a good stability with caustic solutions and acids. It is especially suited for formulations based on sodium hydroxide or phosphoric acid. |
| Cognis - Care Chemicals | DEHYPOUND ® ADVANCED | DEHYPOUND ® ADVANCED. is a NO-VOC low foaming synergistic surfactant blend designed for hard surface cleaning. It possesses a great wetting property and exhibits a low foam even when in agitated or pumped washing liquors. |
| Cognis - Care Chemicals | DEHYPOUND ® ST 15 | DEHYPOUND ® ST-15 is a non-ionic defoaming surfactant that provides foam control and enhances cleaning performance. |
| Cognis - Care Chemicals | DEHYTON ® AB 30 | DEHYTON ® AB-30, INCI: Coco Betaine, is a fatty amine derivaive with a betaine structure. DEHYTON ® AB30 is a well compatible amphoteric surfactant suitable for the application in neutral as well as acidic and highly alkaline cleaners, shampoos and body cleansing preparations. |
| Cognis - Care Chemicals | DEHYTON ® AB 30 | DEHYTON ® AB-30, INCI: Coco Betaine, is ECOCERT approved, natural in origin and is a fatty amine derivaive with a betaine structure. DEHYTON ® AB30 is a well compatible amphoteric surfactant suitable for the application in neutral as well as acidic and highly alkaline cleaners, shampoos and body cleansing preparations. |
| Cognis - Care Chemicals | DERIPHAT ® 160C | DERIPHAT ® 160 C is an amphoteric surfactant of Monosodium N-Lauryl-beta-Iminodipropionic Acid for cleaners. This product exhibits good foaming in hard and soft water. It can be combined with cationic surfactants which are often used as bactericides or fungicides for disinfectants. Due to it's amphoteric nature it provides good solubility over a braod range of PH. |
| Cognis - Care Chemicals | GLUCOPON ® 215 CS UP | GLUCOPON ® 215 CS UP, INCI: Capryl Glucoside is a GRAS approved green surfactant that exhibits caustic stability and solubility in caustic and saline solutions. Due to its good wetting and dispersing properties it can be used for caustic, neutral and acidic hard surface cleaning for house and institutional sector. GLUCOPON ® 215 CS UP shows excellent solubilizing properties in highly concentrated surfactant solutions also in the presence of salt and alkalies. |
| Cognis - Care Chemicals | GLUCOPON ® 225 DK | GLUCOPON ® 225 DK, INCI: Decyl Glucoside, is a GRAS approved green surfactant that exhibits excellent caustic solubility and acts as a dispersant and wetting agent. It may also be used as a coupling agent in high caustic or high electrolyte solutions. It is compatible with all other classes of surface active agents and is completely biodegradable. Mainly used for hard surface cleaning, bottle washing and CIP. |
| Cognis - Care Chemicals | GLUCOPON ® 425 N | GLUCOPON ® 425-N, INCI: Coco-Glucoside, has the wetting, penetration and detergency property desired for products designed to clean metals, glass, ceramics and plastic. It's benefits include non-streaking, non-filming and non-cracking of cleaned surfaces as well as low toxicity. This product is preserved with gluteraldehyde and both the APG and preservative portions are GRAS approved individually. |
| Cognis - Care Chemicals | GLUCOPON ® 600 UP | GLUCOPON ® 600UP, INCI: Lauryl Glucoside, is a GRAS approved green surfactant. The foam behavior of anionic surfactants can be positively affected by adding alkyl polyglucosides. GLUCOPON ® 600 CS UP has the wetting, penetration and detergency property desired for products designed to clean metals, glass, ceramics and plastic. Alkyl polyglucosides represent technology advantages in manufacture of mild dish washing agents combined with cleaning performance. |
| Cognis - Care Chemicals | GLUCOPON ® 625 UP | GLUCOPON ® 625 UP, INCI: Lauryl Glucoside, is a GRAS approved green surfactant that has the wetting, penetration and detergency property desired for laundry detergents, liquid hand dish detergents & I & I cleaners. It functions as a conventional non-ionic surfactant but is easy to formulate, because it will not gel upon dilution. |
| Cognis - Care Chemicals | PLANTAPON ® 611L | PLANTAPON ® 611L, INCI: Sodium Laureth Sulfate & Lauryl Glucoside & Cocamidopropyl Betaine, is an alkanolamide free, very mild, high active surfactant concentrate containing alkyl glucosides. It is a combination of high foaming sodium laureth sulfate, a cocamideopropyl betaine and a laural glucoside designed to build high viscosity at low active levels. PLANTAPON ® 611L can be diluted to yield high foaming, shampoos, body washes, skin cleaners as well as hand dish and delicate fabric wash liquids. Contains Sodium Laureth Sulfate, Cocamidopropyl Betaine and Lauryl-Glucoside. |

D. BASIC REAGENTS

Although chlorhexidine or a chlorhexidine derivative may be included in various antimicrobial compositions presented herein, it is anticipated that one or more basic reagents that exhibit an antimicrobial property may be substituted for, or used in combination with, chlorhexidine. It is anticipated that certain guanidium compounds, such as alexidine or hexamidine may be substituted for or used in combination with chlorhexidine. The basic reagent can be an alkyl or aryl oxide, thiol, sulfide, phosphorous, aliphatic or aromatic amine, guanidinium compound or a halide such as $F^-$, $Br^-$ and $I^-$. Some examples of the basic reagents that can be used include phenoxide antiseptics (such as clofoctol, chloroxylenol, triclosan) or guanidium compounds (such as chlorhexidine, alexidine, hexamidine) or bipyridines (such as octenidines).

Other examples include a guanidium compound, a biguanide, a bipyridine, a phenoxide antiseptic, an alkyl oxide, an aryl oxide, a thiol, a halide, an aliphatic amine, or an aromatic amine. Non-limiting examples of guanidium compounds include chlorhexidine, alexidine, and hexamidine. In other specific embodiments, the basic reagent is a bipyridine. One example of a bipyridine is octenidine. In yet other aspects, the basic reagent is a phenoxide antiseptic.

E. CHELATORS AND/OR ANTICOAGULANTS

A chelate is the type of coordination compound in which a central metal ion is attached by coordinate links to two or more nonmetal atoms in the same molecule. Heterocyclic rings are thus formed during chelation, with the metal atom as part of the ring. The molecule comprising the nonmetal linking atoms is termed a chelator. Chelators are used in various chemical applications, for example as titrating agents or as metal ion scavengers. Chelators can be used to remove ions from participation in biological reactions. For example, the well-known chelator ethylenediamine-N,N,N',N',-tetraacetic acid (EDTA) acts as an anticoagulant because it is capable of scavenging calcium ions from the blood.

It has been previously shown that chelators have significant growth inhibitory effect against several microbes. It is known that iron and other trace metals are essential in the life cycle of microorganisms such as fungi and bacteria. Without these trace metals, microbes are unable to grow and reproduce. Although iron is abundant in nature, its availability for microbial assimilation is limited owing to the insolubility of ferric ions at neutral or alkaline pH. As a consequence, many microbes have evolved their own specialized trace metal-scavenging molecules, called siderophores, which bind with trace metals and make them available for uptake by the microbes. The chelators used in conjunction with the present invention provide an inhibitory effect upon microbial pathogens by competing with the siderophores for any available trace metal ions. In this way, the chelators present in the pharmaceutical preparations of the present invention "steal" the metal ions essential for microbial growth, effectively causing the microbe to "starve to death." The additional antibiotic agents and the ethanol of the compositions of the present invention then come in and attack the weakened microbe, thereby destroying them or inhibiting their growth.

Table 2 below provides a representative list of chelators useful in conjunction with the present invention. However, the list provided in Table 2 is not meant to be exhaustive. Some useful chelators are those which bind trace metal ions with a binding constant ranging from $10^1$ to $10^{100}$. More preferred chelators are those which bind trace metal ions with a binding constant ranging from $10^{10}$ to $10^{80}$; and most preferred chelators are those which bind trace metal ions with a binding constant ranging from $10^{15}$ to $10^{60}$. Furthermore, preferred chelators are those which have been shown to have an inhibitory effect upon target microbial pathogens, for example the disodium salt of EDTA.

TABLE 2

| Chelators | |
|---|---|
| Abbreviation | Full Name |
| EDTA free acid | Ethylenediamine-N,N,N',N',-tetraacetic acid |
| EDTA 2Na | Ethylenediamine-N,N,N',N',-tetraacetic acid, disodium salt, dihydrate |
| EDTA 3Na | Ethylenediamine-N,N,N',N',-tetraacetic acid, trisodium salt, trihydrate |
| EDTA 4Na | Ethylenediamine-N,N,N',N'-tetraacetic acid, tetrasodium salt, tetrahydrate |
| EDTA 2K | Ethylenefisminr-N,N,N',N'-tetraacetic acid, dipotassium salt, dihydrate |
| EDTA 2Li | Ethylenediamine-N,N,N',N'-tetraacetic acid, dilithium salt, monhydrate |
| EDTA $2NH_4$ | Ethylenediamine-N,N,N',N'-tetraacetic acid, diammonium salt |
| EDTA 3K | Ethylenediamine-N,N,N',N'-tetraacetic acid, tripotassium salt, dihydrate |
| Ba(II)-EDTA | Ethylenediamine-N,N,N',N'-tetraacetic acid, barium chelate |
| Ca(II)-EDTA | Ethylenediamine-N,N,N',N'-tetraacetic acid, calcium chelate |
| Ce(III)-EDTA | Ethylenediamine-N,N,N',N'-tetraacetic acid, cerium chelate |
| Co(II)-EDTA | Ethylenediamine-N,N,N',N'-tetraacetic acid, cobalt chelate |
| Cu(II)-EDTA | Ethylenediamine-N,N,N',N'-tetraacetic acid, copper chelate |
| Dy(III)-EDTA | Ethylenediamine-N,N,N',N'-tetraacetic acid, dysprosium chelate |
| Eu(III)-EDTA | Ethylenediamine-N,N,N',N'-tetraacetic acid, europium chelate |
| Fe(III)-EDTA | Ethylenediamine-N,N,N',N'-tetraacetic acid, iron chelate |
| In(III)-EDTA | Ethylenediamine-N,N,N',N'-tetraacetic acid, indium chelate |
| La(III)-EDTA | Ethylenediamine-N,N,N',N'-tetraacetic acid, lanthanum chelate |
| Mg(II)-EDTA | Ethylenediamine-N,N,N',N'-tetraacetic acid, magnesium chelate |
| Mn(II)-EDTA | Ethylenediamine-N,N,N',N'-tetraacetic acid, manganese chelate |
| Ni(II)-EDTA | Ethylenediamine-N,N,N',N'-tetraacetic acid, nickel chelate |
| Sm(III)-EDTA | Ethylenediamine-N,N,N',N'-tetraacetic acid, samarium chelate |
| Sr(II)-EDTA | Ethylenediamine-N,N,N',N'-tetraacetic acid, strontium chelate |
| Zn(II)-EDTA | Ethylenediamine-N,N,N',N'-tetraacetic acid, zinc chelate |
| CyDTA | trans-1,2-Diaminocyclohexane-N,N,N',N'-tetraaceticacid, monohydrate |
| DHEG | N,N-Bis(2-hydroxyethyl)glycine |
| DTPA-OH | 1,3-Diamino-2-hydroxypropane-N,N,N',N'-tetraacetic acid |
| DTPA | 1,3-Diaminopropane-N,N,N',N'-tetraacetic acid |
| EDDA | Ethylenediamine-N,N'-diacetic acid |
| EDDP | Ethylenediamine-N,N'-dipropionic acid dihydrochloride |
| EDDPO | Ethylenediamine-N,N'-bis(methylenephosphonic acid), hemihydrate |
| EDTA-OH | N-(2-Hydroxyethyl)ethylenediamine-N,N',N'-triacetic acid |
| EDTPO | Ethylenediamine-N,N,N',N'-tetrakis(methylenephosponic acid) |
| EGTA | O,O'-bis(2-aminoethyl)ethyleneglycol-N,N,N',N'-tetraacetic acid |

TABLE 2-continued

| Chelators | |
|---|---|
| Abbreviation | Full Name |
| HBED | N,N-diacetic acid |
| HDTA | 1,6-Hexamethylenediamine-N,N,N',N'-tetraacetic acid |
| HIDA | N-(2-Hydroxyethyl)iminodiacetic acid |
| IDA | Iminodiacetic acid |
| Methyl-EDTA | 1,2-Diaminopropane-N,N,N',N'-tetraacetic acid |
| NTA | Nitrilotriacetic acid |
| NTP | Nitrilotripropionic acid |
| NTPO | Nitrilotris(methylenephosphoric acid), trisodium salt |
| O-Bistren | 7,19,30-Trioxa-1,4,10,13,16,22,27,33-octaabicyclo [11,11,11] pentatriacontane hexahydrobromide |
| TTHA | Triethylenetetramine-N,N,N',N'',N''',N'''-hexaacetic acid |

In addition, as several anticoagulants have similar chelating and hence antimicrobial activity, use of anticoagulants such as EGTA, EDTA, heparin, urokinase, streptokinase, low molecular weight heparin, enoxaparin, sodium coumarin, indanedione, anisindione, warfarin, protamine sulfate, anti-thrombin III, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl)amine, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, or glycosaminoglycans etc. is also contemplated in the present invention. Moreover, additional chelators, anticoagulants and/or additional agents useful in the practice of the present invention may be found in U.S. Pat. No. 5,688,516, incorporated herein by reference.

F. ALCOHOLS

The solutions of the instant invention are contemplated to comprise an alcohol, such as an antiseptic or disinfectant alcohol, in certain embodiments. Exemplary alcohols include ethanol, methanol, isopropanol, benzyl alcohol, chlorobutanol, phenylethyl alcohol, 2-bromo-2-nitropropan-1,3-diol, and the like. The present invention contemplates any effective concentration of alcohol, but will typically employ a final alcohol concentration in the range of about 5%-80% (v/v), more preferably in the range of about 10% to about 50%, more preferably in the range of 15% to 40%, more preferably in the range of about 20% to about 30%, with the most preferable being about 25%. Thus, the more preferred concentration of alcohol will include about 5%, 6%, 7%, 8%, 9%, 10%, 15%, 20%, 25%, 30%, 35%, 40%, 45%, 50%, 55%, 60%, 65%, 70%, 75%, or about 80% (v/v) of the alcohol in the preparation of the instant antimicrobial solutions. This includes the use of intermediate concentrations of alcohol such as about 11%, 22.5%, 26% and the like.

Alcohols such as ethanol are long known to have disinfectant properties. In EP1245247 and U.S. Pat. No. 6,350,251, it is reported that the combination of ethanol with EDTA provides a biocidal lock for indwelling medical devices. In contrast, it has also been shown that a combination of ethanol with EDTA is less effective in killing microbes than ethanol alone (Sherertz et al., 2002). Thus, the art is in a flux about the exact role of the combination of ethanol with EDTA.

The present inventor has shown that ethanol alone, while requiring only a relatively short duration of contact, is only partially effective in killing or controlling microbes on the surface of an indwelling medical device or other surface. In contrast, a combination of an antimicrobial agent and a chelator such as EDTA may be effective, yet it requires a somewhat longer duration of contact (e.g., sometimes on the order of 4 hours). However, in the present invention it is shown that certain embodiments provide unexpectedly effective anti-microbial properties in a very short duration and in addition to eradicating microbes rapidly from a surface they also preventing re-growth of the microbial pathogen on the surface. An additional advantage for the combination, as shown in the studies set forth herein below, is that it is effective at eradicating a broader range of microbial organisms (bacteria and fungi), even at the shorter durations of contact with the treated surface.

G. ADDITIONAL AGENTS

It is also contemplated that any additional pharmacologically active ingredients or sterilization agents may be comprised in the solutions of the present invention or may be used separately for flushing or treating the devices of the present invention to further reduce or eliminate pathogenic microbes and viruses. Typical pharmacologically active ingredients include antifibrin agents, anti-thrombotic agents, and anti-inflammatory agents. Anti-inflammatory agents include steroids, and nonsteroidal anti-inflammatory agents, and salicylates. Anti-thrombotic drugs including acetylsalicylic acid, dipyridamole, heparin, ibuprofen, indomethacin, prostaglandins, sulfinpyrazone, warfarin, thrombolytic enzymes such as streptokinase, urokinase, or plasminogen activator. Complexing agents such as ammonium-1-pyrrolidine dithiocarbanate may also be used. However, the above examples are not meant to be limiting.

In certain applications, it will be sufficient to provide a single pharmacologically active ingredient in the device. In other situations, it will be desirable to combine compatible ingredients. For example, it may prove useful to provide an antimicrobial agent along with an anticoagulant and/or an anti-inflammatory agent. In another example, it may prove useful to provide multiple antimicrobial agents with differing target specificities, modes of action or duration, either alone or in combination with anticoagulants or antiinflammatory agents.

H. PACKAGING AND KITS

Described herein are various packaging techniques that may be employed in providing the flush solutions of the invention as part of a commercially available kit. The kit will optionally include an instruction sheet insert to identify how the kit is to be used.

The kit may comprise of one or two or three or more compartments. The components of the kit may be provided in separate compartments or in the same compartment. The components of the kit may be provided separately or mixed. The mixed components may contain two or more components such as a guanidium compound, a glycol ether, and/or no other component, a chelator, alcohol, deoxycholate, or one or more additional components.

One of the packaging options below maintain the ingredients, for example, the antibiotic, such as minocycline, and the chelating agent/anticoagulant, such as EDTA, in an uncombined form. These components are to be combined shortly before use. These packaging options are contemplated to be part of a 2-compartment or three-compartment container system to provide a total volume of about 3 ml of the ready to use preparation. Any compartmentalized container system may be used to package the compositions of the present invention. An exemplary container system is available from Becton Dickinson.

The various compartmentalized embodiments of the present invention as disclosed above, may be provided in a kit form. Such kits would include a container means comprising a volume of diluent, comprising an alcohol optionally diluted if required in a solution such as saline or sterile water, a second (or more) container means comprising one or more antimicrobial or biocide, a third (or more) container means comprising one or more chelating/anticoagulant agent. The dry components may optionally be mixed in one compartment. The addition of the diluent would then be performed immediately prior to use.

The container means of the kits will generally include at least one vial, test tube, flask, bottle, syringe or other container means, into which the antimicrobial/chelator/anticoagulant/alcohol may be placed, and preferably, suitably aliquoted. Where one or more other antimicrobial components are provided, the kit will also generally contain a second, third or other additional container into which this component may be placed. The kits of the present invention will also typically include a means for containing the one or more components and any other reagent containers in close confinement for commercial sale. Such containers may include injection or blow-molded plastic, or glass containers into which the desired vials are retained.

I. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Modifications for Quantitative Germicidal Spray (Based on Quantitative Carrier Test SOP)

Methods

Using the standard method of testing that consists of a modification for the quantitative germicidal spray, which is based on quantitative carrier tests (SOP) that is outlined below, the inventor has compared the present invention disinfectant consisting of low concentration of chlorhexidine (0.06%), with any of the other biocide enhancers (Glucopon® or Dowanol®) to single components or compounds with chlorhexidine or Glucopon® or Dowanol® alone, including control. Below is a description of the modification for quantitative germicidal spray, which is the standard technique required by the Environmental Protection Agency (EPA).

Media/Supplies

Sterile 50 mL centrifuge tubes, pre-filled with 20 mL of desired neutralizer.

Carrier Preparation

Use 3"×1" sterile glass containers. Place each carrier into a sterile Petri plastic dish.

Carrier Inoculation

1. Inoculate each carrier with 10 μL of bacterial or fungal suspension. If a carrier has a frosted end, inoculate the non-frosted end.

2. Using a sterile inoculating needle, spread the inoculum into an approximate 1 cm×1 cm square. Do not let the inoculum spread to the edges of the carrier.

3. Dry the carriers in a 35° C. incubator for 30 min (lids cracked) or 40 min (lids closed).

Carrier Exposure

1. Spray each carrier as specified by the test product. Ensure the inoculated area is thoroughly covered. Because of the time it takes to transfer the carrier into the neutralizer, a 30-second (or longer) interval time is recommended.

2. After the specified exposure time, transfer each carrier to a pre-filled centrifuge tube using forceps. Be sure to pick up the carrier by the non-inoculated end and place the inoculated end into the neutralizer.

3. Immediately close the cap and invert the tube several times (10 should be sufficient) so the neutralizer coats the entire carrier.

4. From this point on, follow the enumeration procedure as specified in the Quantitative Carrier Test SOP. Note: when calculating total CFU, keep in mind that 20 mL of neutralizer is used, vs. 10 mL in QCT. Adjust calculation accordingly.

Experiment Set 1: Comparing triple combinations of CHG+EDTA+EtOH to CHG alone or CHG+EtOH Objective:

The aim of these sets of experiments is to compare the activity of these various solutions on a 10-set slid carriers of MRSA using standard EPA quantitate carrier test in 25-50% calf serum. According to a scale derived from the EPA standards, we have established that for a disinfectant to be highly effective, it should completely kill the MRSA on 9 out of 10 of the carriers and the 1 out of 10 positive carriers should involve at least 99% reduction in CFU.

Specific Methods:

Glass carriers were inoculated with 10 μL of $1.5\times10^6$ CFU of MRSA in 25% calf serum, mixed together and slides were dried at 37° C. for 40 minutes according to the qualitative protocol outlined above. Sets of 10 carriers were then sprayed with each solution (control—nothing added; 0.06% CHG+4% Glucapon®, 0.06% CHG+3% Dowanol®, 4% Glucopon®+3% Dowanol, 0.06% CHG alone, 4% Glucopon® alone, 3% Dowanol® alone) for one minute, independently. After the exposure, time slides were immersed in 20 mL of D/E neutralizing broth to stop all antiseptic activity. To enumerates antimicrobial activity 500 μL of neutralizing broth was cultured from the 20 mL and spread on Trypticase Soy Agar with 5% sheep blood. Plates were incubated inverted at 37° C. overnight and counted for growth.

Results and Conclusions

Experiment Set 1: Comparing combinations of CHG+Glucopon® or CHG+Dowanol® to other components or combinations (See Table 3 and FIG. 1).

TABLE 3

| Experiments at One Minute | | | | | | | |
|---|---|---|---|---|---|---|---|
| Slide Carrier | Control | 0.06% CHG + 4% Glu | 0.06% CHG + 3% DPnB | 4% Glu + 3% DPnB | 0.06% CHG alone | 4% Glu alone | 3% DPnB alone |
| Number of colonies Detected | | | | | | | |
| 1 | 1.20E+04 | 0 | 0 | 280 | 0 | 40 | 5.2E+02 |
| 2 | 8.20E+03 | 0 | 0 | 120 | 0 | 0 | 8.8E+02 |
| 3 | 9.00E+03 | 0 | 0 | 40 | 40 | 0 | 7.2E+02 |
| 4 | 7.20E+03 | 0 | 0 | 320 | 2.3E+04 | 280 | 9.6E+02 |
| 5 | 9.10E+03 | 0 | 0 | 1.00E+3 | 200 | 80 | 2.12E+03 |
| 6 | 3.50E+04 | 0 | 0 | 360 | 0 | 40 | 6.00E+02 |
| 7 | 3.50E+04 | 0 | 0 | 5.6E+02 | 0 | 0 | 1.20E+02 |
| 8 | 4.6E+04 | 0 | 40 | 480 | 0 | 80 | 1.12E+03 |
| 9 | 4.9E+04 | 0 | 0 | 8.00E+02 | 0 | 80 | 9.20E+02 |
| 10 | 3.00#+04 | 0 | 0 | 120 | 160 | 40 | 2.4E+02 |

CGH = chlorhexidine;
DPnB = Dowanol ® gluconate

As shown above, only the combinations comprising CHG+Glucopon® or CHG+Dowanol® passed the test of being highly effective against MRSA as a form of a resistant bacteria with 10 out of 10 carriers being negative with CHG+Glucopon® and 9 out of 10 carriers being negative with CHG+Dowanol®, whereby the only one positive carrier showed >99% reduction in colonies.

Conclusions:

1) The combination of low concentration of chlorhexidine plus either Glucopon® or Dowanol® were the only combinations that passed the test and completely killed resistant MRSA (as a form of Gram-positive bacteria). The killing occurred rapidly within 60 seconds of contact time.

2) Chlorhexidine alone failed the test and so do Glucopon® and Dowanol®. Furthermore, the combination of Glucopon® and Dowanol® completely failed the test.

3) Hence, Glucopon® or Dowanol® act as bioenhancers of chlorhexidine leading to complete and rapid eradication of MRSA. These surfactants/detergents do not eradicate resistant bacteria on their own (either alone or in combination) but rather enhance the activity of low concentration chlorhexidine. The same is true for deoxycholate. Thus, in certain embodiments the present invention regards the combination of guanidium compounds with surfactants or detergents such as Glucapon®, Dowanol®, or deoxycholate.

Example 2

Dowanol® as Bioenhancer of Chlorhexidine to Achieve a Rapid Kill Against MRSA Current antiseptics and disinfectants (chlorine bleach, phenolics, and quaternary ammoniums) are associated with health risks to personnel and hazardous properties (flammable, volatile, corrosive, etc.). Recently, 2% chlorhexidine with 70% ethanol has been successfully used as a surgical antiseptic. Dowanol® is a glycol ether which is non volatile and could serve as an alternative to ethanol. In this study Dowanol® and Glucopon® (a non ionic surfactant) were examined as bioenhancers of chlorhexidine in achieving rapid kill of resistant bacteria and fungi. A modification of the quantitative germicidal spray (SOP method) was used for testing antiseptics and disinfectants whereby 10 slide carriers were inoculated with $10^5$ (in 50% calf serum) of MRSA, VRE, multidrug-resistant (MDR) *Acinetobacter* (ACN), MDR *Pseudomonas aeruginosa* (PSA) and fluconazole-resistant *Candida glabrata* (CG), and then they were exposed briefly (1 minute) to the antiseptics. The inventor used 0.06% chlorhexidine (CHG), 4% Glucopon®, 5% Dowanol® alone or in combination. After the exposure time slides were immersed in 20 ml of neutralizing broth to stop all antiseptic activity, plates were incubated, inverted at 37° overnight and counted for growth. Efficacious agents were those that achieved complete kill with >99.9% reduction in colonies in 10 out 10 carriers. For results, 5% Dowanol® in combination with 0.6% CHG achieved complete kill against all organisms tested within 1 minute. See results below for MRSA. When 3% Dowanol® was used combined with 0.06% CHG and 4% Glucopon®, a complete kill was achieved for all MDR organisms. Thus, 5% Dowanol® serves as a bioenhancer for chlorhexidine resulting in rapid kill of MDR organisms, in particular embodiments of the invention.

Further details are provided below. Using the standard quantitative germicidal spray, which is based on quantitative carrier tests (SOP), the inventor has compared the activity of certain embodiments of the novel present inventive disinfectant against MRSA, VRE, MDR-*P. aeruginosa* and *Acinetobacter baumanni*, for example. The novel disinfectant consisted of low concentration of chlorhexidine (0.06% CHX) plus Dowanol® with or without Glucopon® and it was compared to the other surfactants or biocide enhancers (Glucopon® and/or Dowanol®) as single components or in combination with chlorhexidine (0.06%), as well as control. Below is a brief description of the experiments performed.

Figure 2:
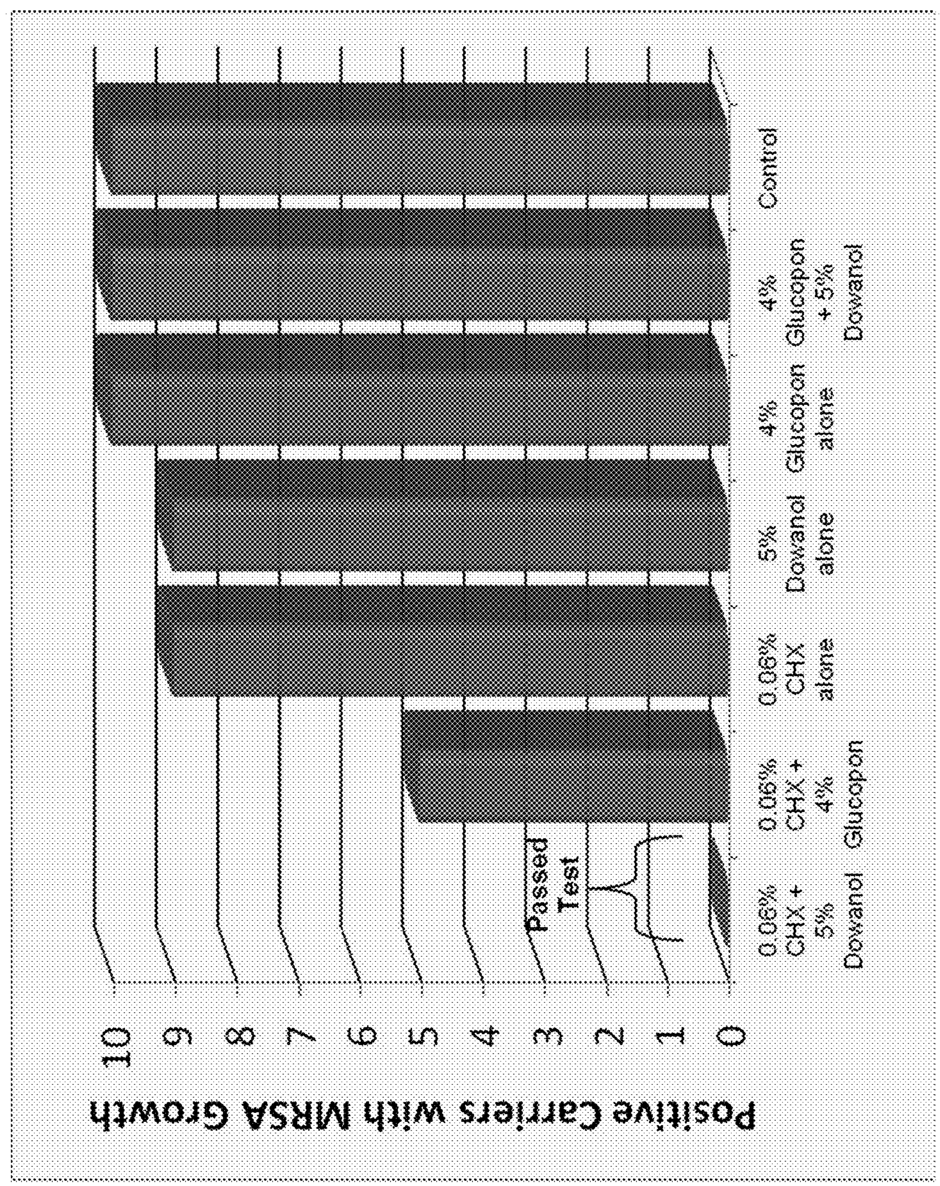
FIG. 2 compares certain exemplary triple combinations of CHX+Dowanol®+Glucopon® to other components or combinations, with exposures of 1 minute.
Figure 3A:
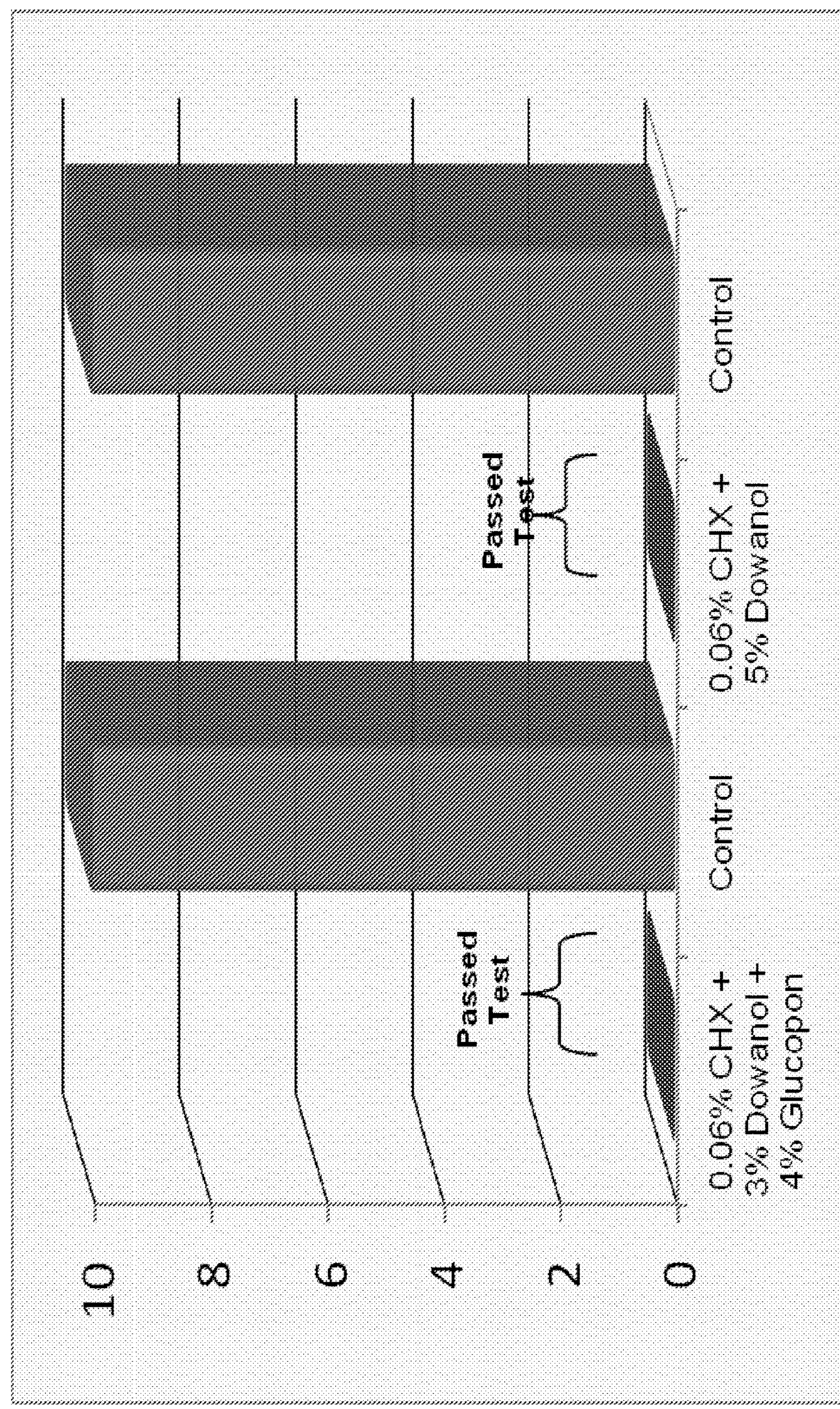
FIGS. 3A-3C compare the activity of combinations of 0.06% CHX+Dowanol® with and without 4% Glucopon® against various resistant gram-positive (VRE) (FIG. 3A) and gram-negative bacteria (e.g., *Pseudomonas aeruginosa* (FIG. 3B) and *Acinetobacter baumanni* (FIG. 3C).
Figure 3B:
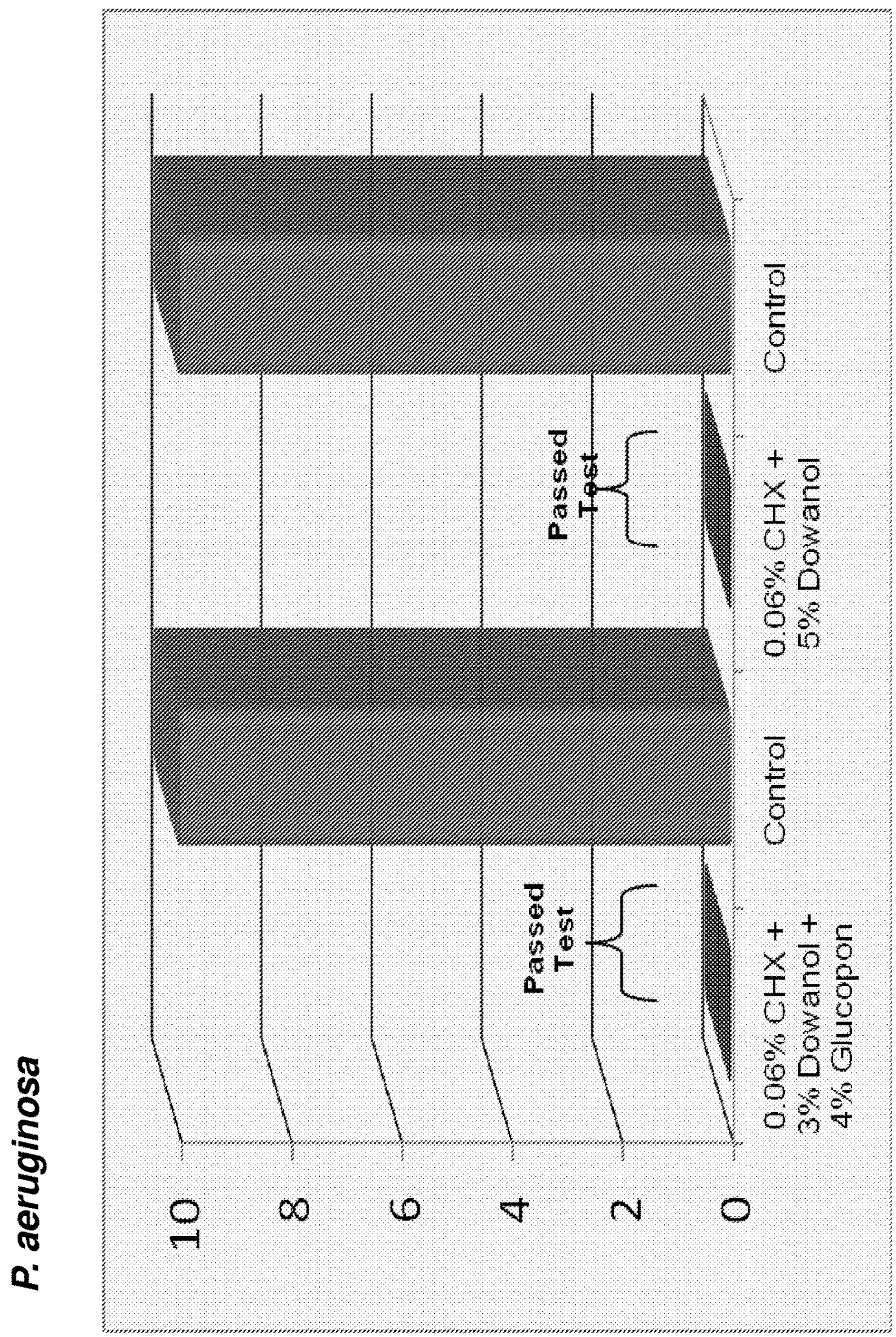
Figure 3C:
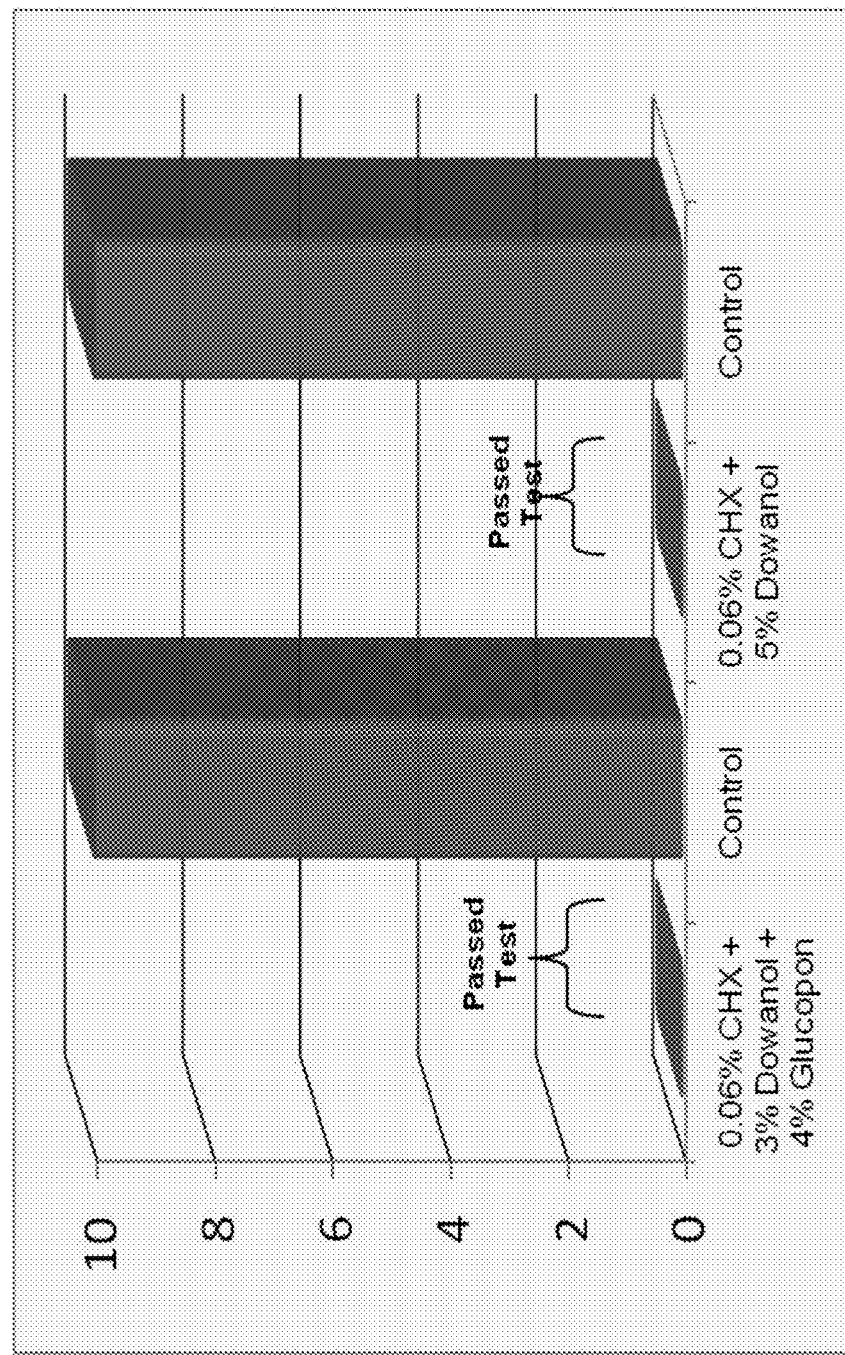

Glass slides were inoculated with 10 uL of $1.5\times10^6$ CFU of bacteria tested in 50% Calf Serum, mixed together, and slides were dried at 37° C. for 40 minutes according to the quantitative carrier test method outlined above. Sets of ten carrier slides were then sprayed with each solution (control—nothing added, 0.06% CHX+4% Glucopon®, 0.06% CHX+5% Dowanol®, 4% Glucopon®+5% Dowanol®, 0.06% CHX alone, 4% Glucopon®, 5% Dowanol® alone) for one minute, independently. A similar experiment was performed whereby 3% Dowanol® replaced 5% Dowanol® and the triple combination of 0.06% CHX+4% Glucopon® with 3% Dowanol® were used (FIG. 2). After the exposure, time slides were immersed in 20 mL of D/E neutralizing broth to stop all antiseptic activity. To enumerate antimicrobial activity 500 uL of neutralizing broth was cultured from the 20 mL and spread on Trypticase Soy Agar with 5%

Sheep blood. Plates were incubated inverted at 37° C. overnight and counted for growth.

EXPERIMENT SET 1: Comparing combinations of CHX+Glucopon® or CHX+Dowanol® to other components or combinations, with experimental exposure lasting 1 minute. As shown in FIG. 1, only the combinations consisting of CHX+Dowanol® passed the test of being highly effective against MRSA (as a form of a resistant bacteria) with 10 out of 10 carriers being negative for CHX+Dowanol® showing rapid >99.9% reduction in colonies after only 1 minute of exposure. Thus, in particular embodiments of the invention, the surfactant Glucopon® acts as a booster of chlorhexidine plus low concentration of Dowanol® leading to complete and rapid eradication of MRSA. These surfactants/detergents do not eradicate resistant bacteria on their own but rather enhance the activity of low concentration chlorhexidine in combination with low concentrations of Dowanol®. The same is true for deoxycholate, in particular aspects of the invention.

EXPERIMENT SET 2: Comparing the triple combinations of CHX+Dowanol®+Glucopon® to other components or combinations: (See FIG. 2), with experimental exposure lasting one minute. As shown in FIG. 2, only the combinations consisting of low concentration CHX+low concentration Dowanol®+Glucopon® passed the test of being highly effective against MRSA as a form of a resistant bacteria with 10 out of 10 carriers being negative for showing rapid >99.9% reduction in colonies after only 1-minute of exposure.

EXPERIMENT SET 3: Comparing the activity of combinations of 0.06% CHX+Dowanol® with and without 4% Glucopon® against various resistant gram-positive (VRE) and gram-negative bacteria (e.g., *Pseudomonas aeruginosa* and *Acinetobacter baumanni.*

Thus, Dowanol® acts as a bioenhancer of chlorhexidine leading to complete and rapid eradication of MRSA. This bioenhancer does not eradicate resistant bacteria on its own but rather enhances the activity of low concentration chlorhexidine. In addition, the surfactant Glucopon® acts as booster of chlorhexidine plus low concentration of Dowanol® leading to complete and rapid eradication of MRSA.

Example 3

Efficacy of Antiseptic Environmental Solution Containing 0.5% CHG+3% CaEDTA+(5% or 10%) ETOH with or without 4% Glucopon The present Example concerns determination of the optimal concentration of EtOH to be added to the antiseptic environmental solution and to determine whether the addition of 4% Glucopon® enhances this efficacy. Efficacy of various combinations of 0.5% chlorhexidine digluconate (CHG)+3% CaEDTA+5 or 10% EtOH with our without 4% Glucopon® were tested using a modification of the standard operating procedure (SOP) for quantitative evaluation of germicidal spray. Ten microscope slides were inoculated independently with 20 uL of 4 multidrug resistant (MDR) organisms at a concentration of $1\times10^5$ CFU/mL in 50% calf serum. Organisms tested include methicillin resistant *Staphylococcus aureus* (MRSA 4798), Vancomycin resistant entercocci (EN 3868), MDR-*Pseudomonas aeruginosa* (PS 4689), and *Candida albicans*. Slides were placed in covered sterile Petri dishes and dried at 37° C. for 1 hour to ensure complete drying. Samples were then briefly exposed (1 minute) to antiseptic environmental solutions. After exposure slides were immediately immersed in 20 mL of D/E Neutralizing Broth, capped, and shaken by hand in order to ensure thorough covering by the neutralizing broth to stop all antiseptic activity. Resulting broth was then serially diluted and spread on agar plates, Trypticase Soy Agar with 5%. Sheep blood for bacterial organisms and Sauboard Dextrose agar for yeast organisms. Plates were incubated inverted at 37° C. overnight and counted for growth. Efficacious agents were those that achieved kill with >99.9% reduction in growth, compared to control, in at least 8 out of 10 carriers.

Exemplary organisms tested included Methicillin resistant *Staphylococcus aureus* (MRSA 4798), Vancomycin-resistant entercocci (VRE 3868), MDR—*Pseudomonas aeruginosa* (PS 4689), and *Candida albicans*. Exemplary solutions tested included 0.5% CHG+3% CaEDTA+10% EtOH; 0.5% CHG+3% CaEDTA+10% EtOH+4% Glucopon; 0.5% CHG+3% CaEDTA+5% EtOH; and 0.5% CHG+3% CaEDTA+5% EtOH+4% Glucopon®.

Figure 4:
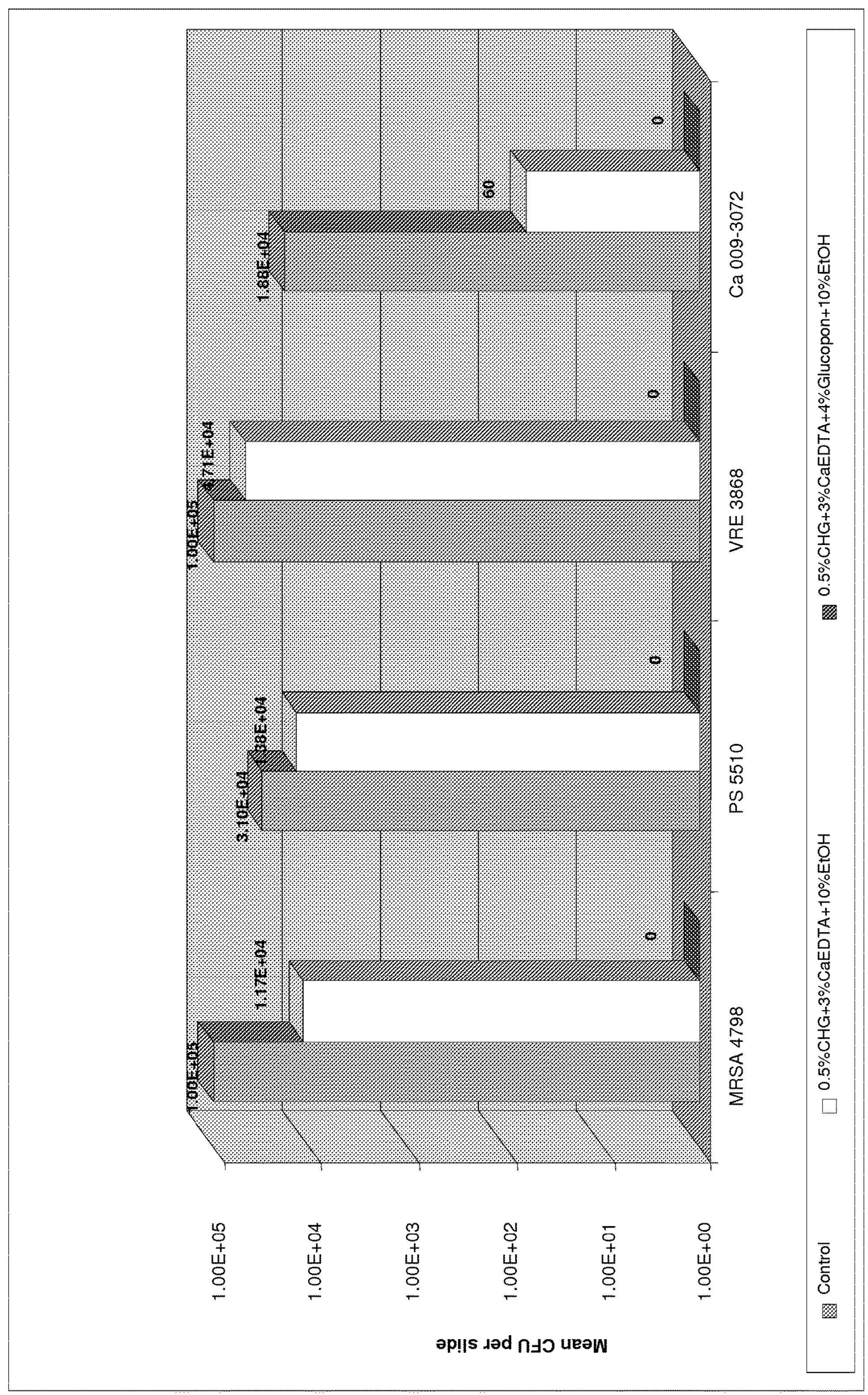
FIG. 4 shows efficacy of environmental solution containing 0.5% CHG, 3% CaEDTA, and 10% EtOH with and without 4% Glucopon®.
Figure 5:
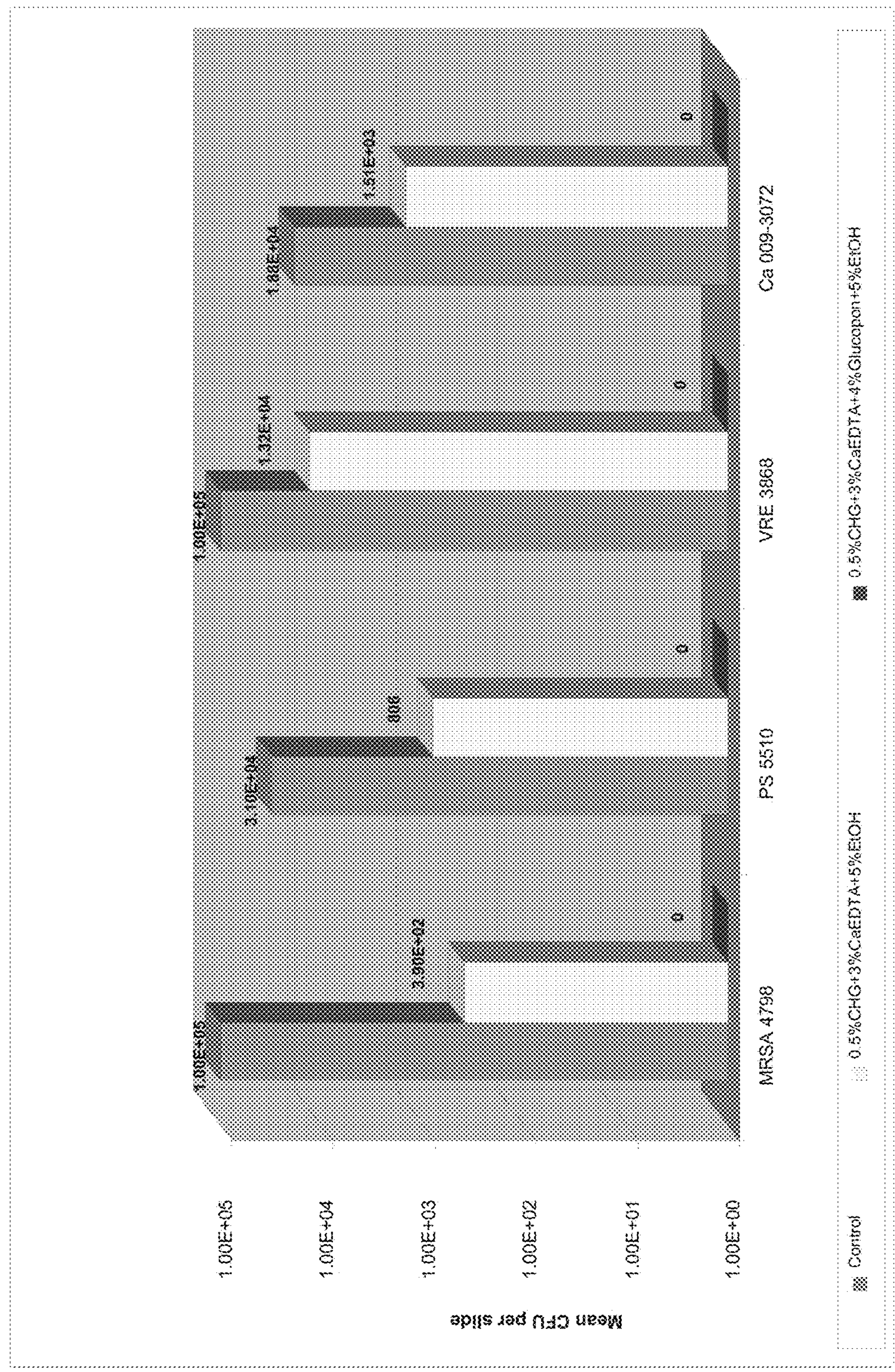
FIG. 5 shows efficacy of environmental solution containing 0.5% CHG, 3% CaEDTA, and 5% EtOH with and without 4% Glucopon®.

FIG. 4 shows efficacy of environmental solution containing 0.5% CHG, 3% CaEDTA, and 10% EtOH with and without 4% Glucopon®. FIG. 5 shows efficacy of environmental solution containing 0.5% CHG, 3% CaEDTA, and 5% EtOH with and without 4% Glucopon®.

Thus, this present Example demonstrates that precipitation occurred upon mixing both the 5% and 10% EtOH solutions without Glucopon®. With the addition of 4% Glucopon® no precipitation occurred. The addition of 4% Glucopon® enhances the environmental solution at both 5% and 10% concentrations of EtOH, for example, to completely eradicate all organisms.

Example 4

Antimicrobial Efficacy of Chlorhexidine Plus 5% Dowanol® or Chlorhexidine Plus 50% Glycerol Lock Solution Against Resistant Bacteria and Fungi in Biofilm Objective:

The aim of experiment set 4 is to test the activity of 5% Dowanol®+Chlorhexidine 0.06% (CHX) or 50% Glycerol+CHX (0.06% or 0.12%) against various resistant bacteria and fungi.

Methods:

Modified Kuhns Biofilm Model:

Biofilm was grown on sterile silicone discs following a modified Kuhn's method. Briefly, silicone discs were placed into a 24 well tissue culture plate and incubated overnight at 37° C. The plasma was then removed and replaced with 1 mL of 5.5×105 CFU/mL inoculum of various organisms. The plates were then incubated for an additional 24 hrs at 37° C. Inoculum was then removed and discs were washed shaking for 30 minutes in 0.9% sterile saline. After washing the discs were placed in 1 mL of various antimicrobial solutions and incubated at 37° C. for 2 hrs. The discs were then removed and placed in 5 mL of 0.9% sterile saline and sonicated to disrupt any remaining biofilm. The resulting solution was then quantitatively cultured by making serial dilutions in 0.9% sterile saline and plating on agar plates, TSA+5% sheep blood for all bacterial organisms and Sabouraud Dextrose Agar for yeasts. A total of 3-9 discs were used for both organisms and respective labs solutions (see Tables 4-6).

Organisms being Tested:

1. Methicillin Resistant *Staphylococcus aureus* (MRSA 4798)

2. MDR—*Pseudomonas aeruginosa* (PS 4689)

3. *Candida glabrata*

Solutions being Tested:

1.5% Dowanol®+0.06% Chlorhexidine digluconate 2.50% Glycerol+0.06% Chlorhexidine digluconate 3.50% Glycerol+0.12% Chlorhexidine digluconate 4.50% Glycerol Alone 5. Control Muller Hinton Broth (MHB)

Results and Conclusions

Figure 6:
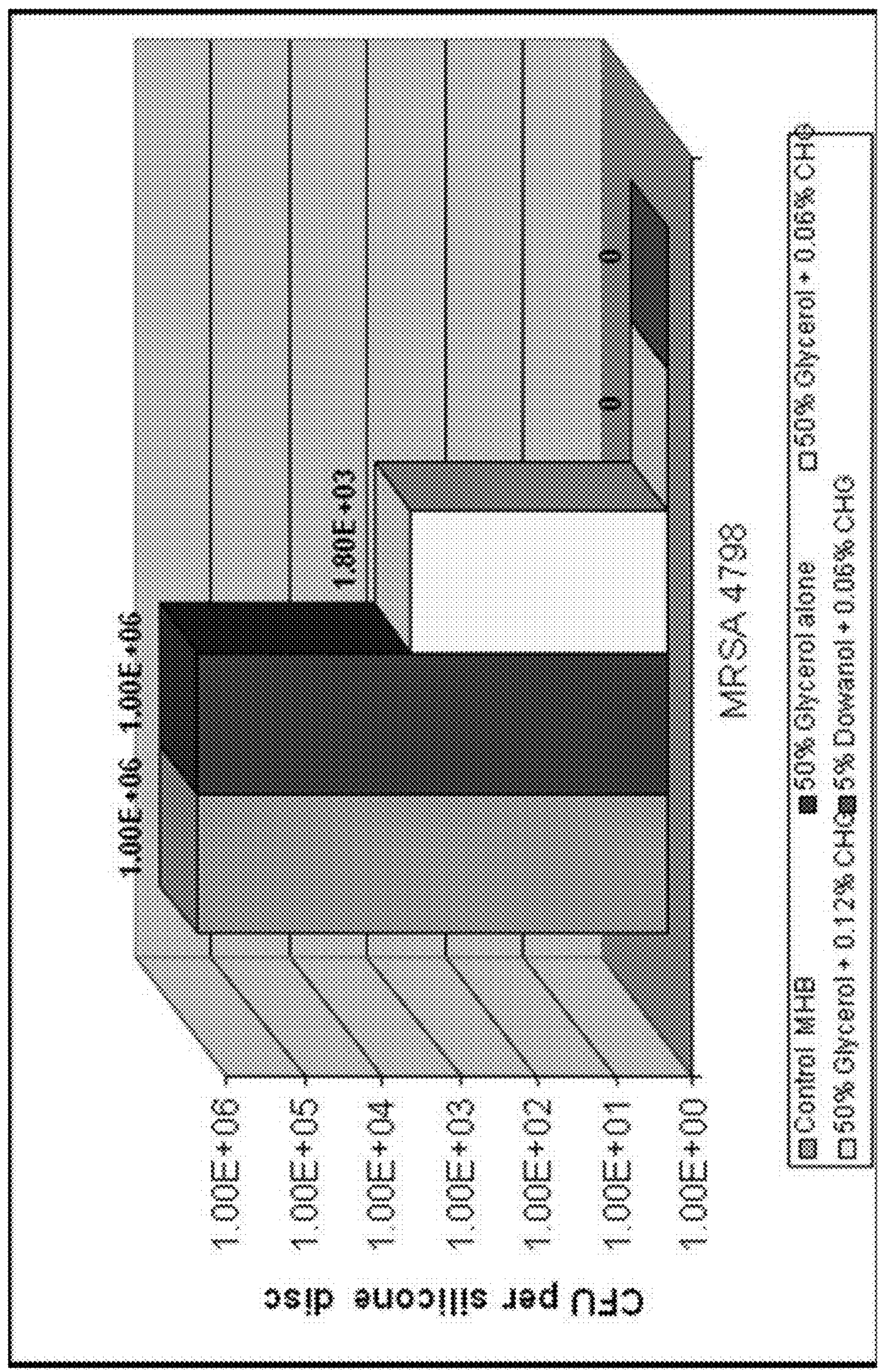
FIG. 6 shows activity of lock solutions against MRSA.
Figure 7:
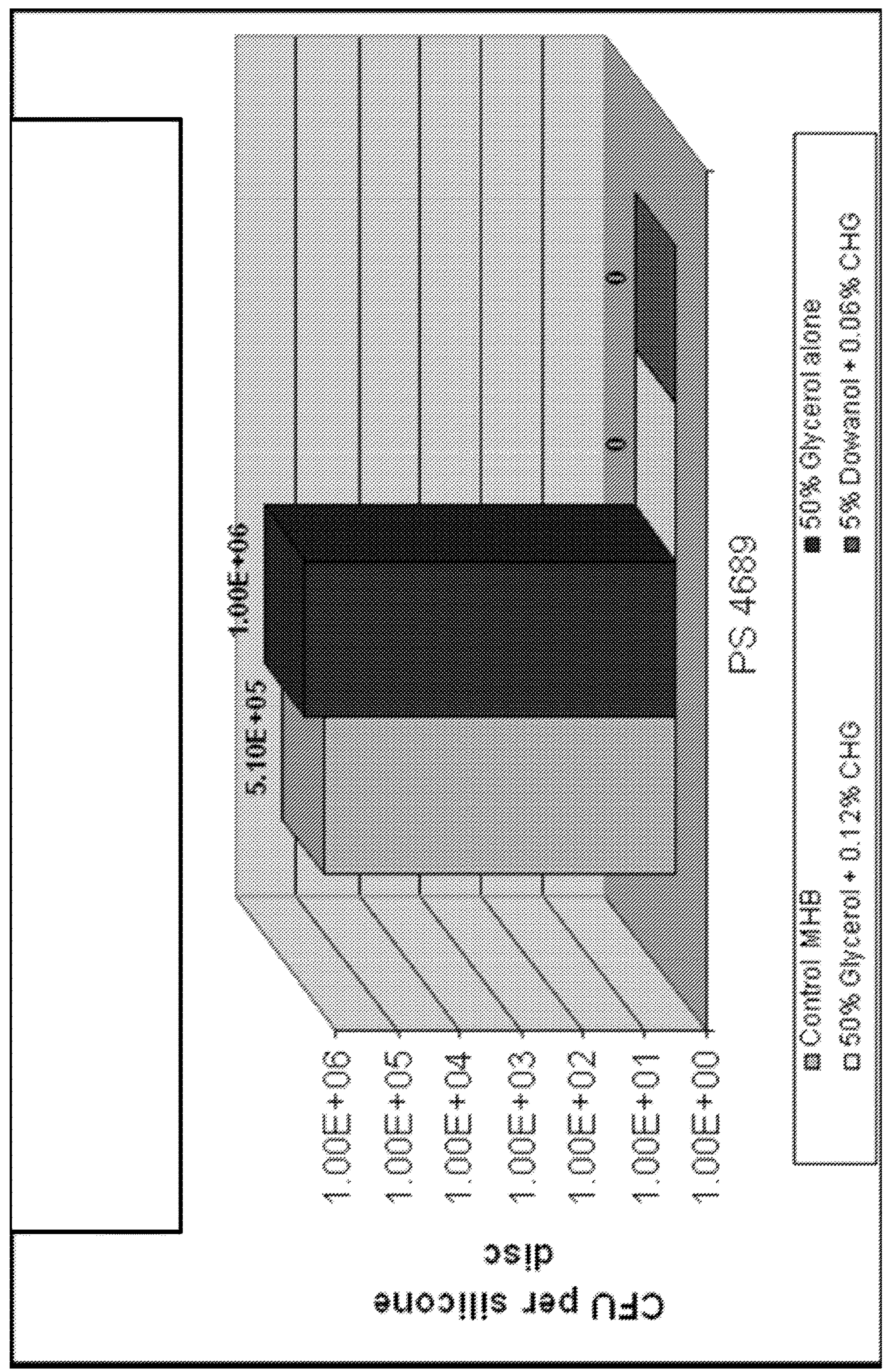
FIG. 7 shows activity of lock solutions against *Pseudomonas aeruginosa.*

FIG. 6 shows activity of lock solutions against MRSA.

TABLE 4

Activity of Lock Solutions against MRSA

| Organism | Treatment | Mean | Median (range) | N | p-value* |
|---|---|---|---|---|---|
| MRSA 4798 | Control MHB | $7.1 \times 10^6$ | $1.0 \times 10^6$ ($1.0 \times 10^6$-$2.9 \times 10^7$) | 9 | |
| | 5% Dowanol ® + 0.06% CHG | $3.0 \times 10^3$ | 0 (0-$1.8 \times 10^4$) | 9 | <.001 |
| | 50% Glycerol + 0.06% CHG | $2.0 \times 10^3$ | $1.8 \times 10^3$ (0-$5.0 \times 10^3$) | 9 | <.001 |
| | 50% Glycerol + 0.12% CHG | $8.5 \times 10^2$ | 0 (0-$5.0 \times 10^3$) | 9 | <.001 |
| | 50% Glycerol alone | $1.0 \times 10^7$ | $1.0 \times 10^6$ ($1.0 \times 10^6$-$2.9 \times 10^7$) | 6 | 0.7 |

Note
*p-value is the result comparing with control cvcs.

Statistical methods: Wilcoxon rank sum tests were used for comparisons. All the analyses were performed using SAS version 9.1 (SAS Institute Inc., Cary, N.C.).

TABLE 5

Activity against Pseudomonas aeruginosa

| Organism | Treatment | Mean | Median (range) | N | p-value* |
|---|---|---|---|---|---|
| PS 4689 | Control MHB | $5.0 \times 10^5$ | $5.1 \times 10^5$ ($4.0 \times 10^2$-$1.0 \times 10^6$) | 6 | |
| | 5% Dowanol ® + 0.06% CHG | 0 | 0 (0-0) | 6 | 0.003 |
| | 50% Glycerol + 0.12% CHG | 0 | 0 (0-0) | 6 | 0.003 |
| | 50% Glycerol alone | $1.0 \times 10^6$ | $1.0 \times 10^6$ ($1.0 \times 10^6$-$1.0 \times 10^6$) | 3 | 0.22 |

Note
*p-value is the result comparing with conrtol cvcs.

Statistical methods: Wilcoxon rank sum tests were used for comparisons. All the analyses were performed using SAS version 9.1 (SAS Institute Inc., Cary, N.C.).

Figure 8:
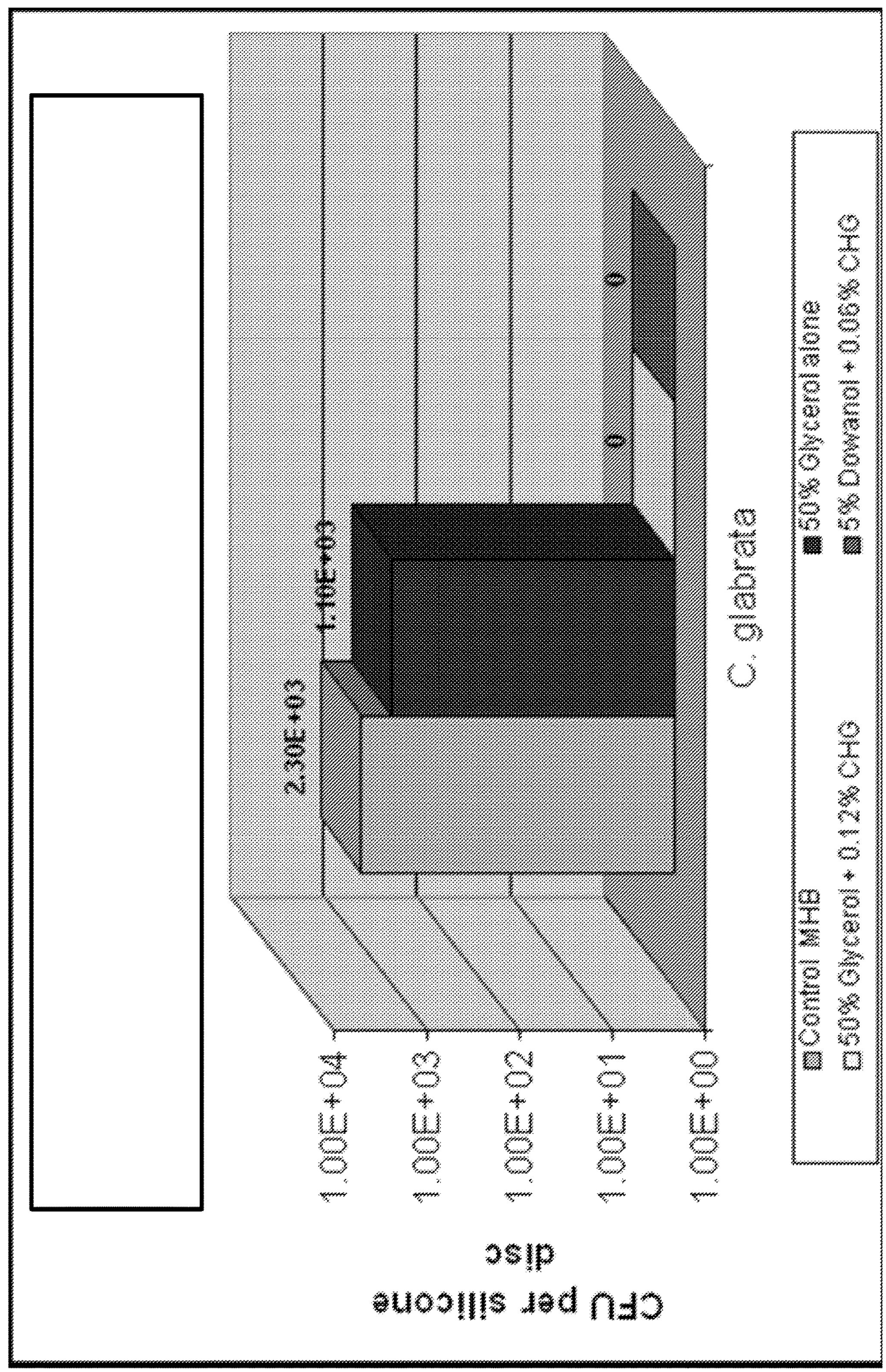
FIG. 8 shows activity of lock solutions against *Candida glabrata.*

FIG. 8 demonstrates activity of lock solutions against *Candida glabrata*.

TABLE 6

Activity against Candida glabrata

| Organism | Treatment | Mean | Median (range) | N | p-value* |
|---|---|---|---|---|---|
| *C. glabrata* | Control MHB | $5.6 \times 10^3$ | $2.3 \times 10^3$ (0-$2.0 \times 10^4$) | 6 | |
| | 5% Dowanol ® + 0.06% CHG | 0 | 0 (0-0) | 6 | 0.01 |
| | 50% glycerol + 0.12% CHG | 0 | 0 (0-0) | 6 | 0.01 |
| | 50% Glycerol alone | $6.2 \times 10^3$ | $1.1 \times 10^3$ ($8.5 \times 10^2$-$1.7 \times 10^4$) | 3 | >.99 |

Note
*p-value is the result comparing with control cvcs.

Statistical methods: Wilcoxon rank sum tests were used for comparisons. All the analyses were performed using SAS version 9.1 (SAS Institute Inc., Cary, N.C.).

Thus, 5% Dowanol® in combination with 0.06% CHX and 50% Glycerol in combination with 0.12% CHX were highly effective in reducing the growth of MRSA in biofilm (>99.9% reduction) and eradicating the growth of *P. aeruginosa* and *Candida glabrata* in biofilm. These combinations could be used in biofilm rich environment such as mouthwash or catheter locks since bacteria and fungi are known to grown in a biofilm in such environments. Dowanol® or Glycerol in combination with chlorhexidine is highly effective against biofilm-forming bacteria and fungi, for example, and such combinations are useful for antimicrobial purposes, such as for mouthwashes, catheter locks and in other biofilm-forming environments.

All of the compositions and/or methods and/or apparati disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparati and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Provisional Patent Application Ser. No. 60/261,447
U.S. Provisional Patent Application Ser. No. 60/316,165
U.S. Non-Provisional patent application Ser. No. 10/044,842
U.S. Pat. No. 4,748,158
U.S. Pat. No. 5,362,754
U.S. Pat. No. 5,688,516
U.S. Pat. No. 6,350,251
Bleyer et al., In: Proceedings of the 4th Decennial International Conference on Nosocomial and Healthcare-Associated Infections in conjunction with the 10th Annual Meeting of the Society for Healthcare Epidemiology of America, Atlanta, Ga., pp 91, 2000.

Carratala et al., *Antimicrob. Agents Chemother.,* 43:2200-2204, 1999.

Centers for Disease Control and Prevention, MMWR 51(RR-10), 2002.

Chatzinikolaou et al., *Clin. Infect. Dis.,* 36(1):116-9 (2003). EP1245247

Evans et al., *Antimicrob. Agents Chemother.,* 31(6):889-894, 1987.

Henrickson et al., *J. Clin. Oncol.,* 18:1269-1278, 2002.

Kuhn et al., *Antimicrob. Agents Chemother.,* 46(6):1773-1780, 2002.

Kluger et al., In: Interscience Conference on Antimicrobial Agents and Chemotherapy (ICAAC) Abstracts of the 39th, 514, 1999.

Maki et al., In: Hospital Infections. Bennett J V, Brachman PS, eds. Lippincott-Raven, Philadelphia, Pa., pp 689-94, 1998.

Mermel et al., *Clin. Infect. Dis.* 32:1249-1272, 2001.

Nickel et al., *Dialogues in Pediatric Urology,* 14(10):7-8, 1991.

Raad et al., *J. Infect. Dis.* 168:400-407, 1993.

Raad et al., *Antimicrob. Agents Chemother.,* 46(2):327-332, 2002.

Raad et al., *Arch. Intern. Med.* 162:871-878, 2002.

Reardon et al., *Medical Laboratory Sciences,* 48:72-75, 1991.

Sherertz et al, In: Proceedings of the 12th Annual Meeting of the Society for Healthcare Epidemiology of America (abstract #52676), Salt Lake City, Utah, Apr. 7-9, 2002.

Schwartz et al., *J. Clin. Oncol.,* 8:1591-1597, 1990.

Spafford et al., *MMWR.,* 44:1-13, 1994.

What is claimed is:

1. An antimicrobial composition comprising (a) a biguanide selected from the group consisting of polyhexamethylene biguanide (PHMB), chlorhexidine, alexidine and hexamidine, (b) a dipropylene glycol n-butyl ether, and EDTA 4Na chelator, in respective amounts effective to eradicate a population of methicillin-resistant *Staphylococcus aureus* using a standard operating procedure (SOP) quantitative germicidal spray test.

2. The composition of claim 1, wherein the composition further an alkylpolyglucoside.

3. The composition of claim 1, wherein the biguanide is chlorhexidine.

4. The composition of claim 1, further comprising an effective amount of deoxycholate.

5. The composition of claim 2, wherein the alkylpolyglucoside is selected from the group consisting of capryl glucoside, decyl glucoside, coco-glucoside, and lauryl glucoside.

6. A method for eradicating drug resistant bacteria on a surface comprising contacting the surface with the composition of claim 1 for at least one minute.

7. The method of claim 6, wherein the composition further comprises an alkylpolyglucoside.

8. The method of claim 6, wherein the biguanide is chlorhexidine.

9. The method of claim 6, further comprising an effective amount of deoxycholate.

10. The method of claim 7, wherein the alkylpolyglucoside is selected from the group consisting of capryl glucoside, decyl glucoside, coco-glucoside, and lauryl glucoside.

11. The method of claim 6, wherein the drug resistant bacteria are selected from the group consisting of MRSA, vancomycin resistant *enterobacter* ("VRE") and multi-drug resistant *P. aeruginosa* and Actinetobacter.

12. The method of claim 11, wherein the drug resistant bacteria are MRSA.

13. A kit for disinfecting a surface, wherein the kit comprises the composition of claim 1.

14. The kit of claim 13, wherein the biguanide and the dipropylene glycol n-butyl ether are contained in separate containers.

15. A syringe, comprising a unit dose of a pharmacologically effective amount of a solution comprising the composition of claim 1.

16. The antimicrobial composition of claim 1, wherein the biguanide is PHMB.

17. The method of claim 6, wherein the biguanide is PHMB.

18. The composition of claim 1, wherein the composition does not include at least one alcohol.

19. The method of claim 6, wherein the composition does not include at least one alcohol.

20. The kit of claim 13, wherein the composition does not include at least one alcohol.

21. The syringe of claim 15, wherein the composition does not include at least one alcohol.

* * * * *

UNITED STATES PATENT AND TRADEMARK OFFICE

CERTIFICATE OF CORRECTION

PATENT NO. : 9,565,857 B2
APPLICATION NO. : 13/821546
DATED : February 14, 2017
INVENTOR(S) : Issam Raad and George Abiaad It is certified that error appears in the above-identified patent and that said Letters Patent is hereby corrected as shown below:

In the Claims

In Claim 1, Column 37, Line 39, insert --(c)-- before "EDTA 4Na".

In Claim 2, Column 37, Line 45, insert --comprises-- between "further" and "an".

Signed and Sealed this
Eighteenth Day of July, 2017

Joseph Matal

Joseph Matal
*Performing the Functions and Duties of the*
*Under Secretary of Commerce for Intellectual Property and*
*Director of the United States Patent and Trademark Office*